United States Patent
McCombe et al.

(10) Patent No.: US 10,226,354 B2
(45) Date of Patent: Mar. 12, 2019

(54) PROSTHESIS

(71) Applicant: NuVasive, Inc., San Diego, CA (US)

(72) Inventors: Peter Francis McCombe, Brisbane (AU); William R. Sears, Warrawee (AU)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/166,098

(22) Filed: May 26, 2016

(65) Prior Publication Data

US 2016/0346094 A1 Dec. 1, 2016

Related U.S. Application Data

(63) Continuation of application No. 14/827,972, filed on Aug. 17, 2015, now Pat. No. 9,375,322, which is a
(Continued)

(30) Foreign Application Priority Data

Apr. 6, 2005 (AU) .................................. 2005901682

(51) Int. Cl.
*A61F 2/44* (2006.01)
*A61B 34/10* (2016.01)
(Continued)

(52) U.S. Cl.
CPC ............ *A61F 2/4425* (2013.01); *A61B 34/10* (2016.02); *A61B 2034/108* (2016.02); *A61F 2/08* (2013.01);
(Continued)

(58) Field of Classification Search
None
See application file for complete search history.

(56) References Cited

U.S. PATENT DOCUMENTS

| | | | |
|---|---|---|---|
| 4,759,766 A | 7/1988 | Buettner-Janz et al. | |
| 5,258,031 A | 11/1993 | Salib et al. | |

(Continued)

FOREIGN PATENT DOCUMENTS

| | | |
|---|---|---|
| AT | 6369 U1 | 9/2003 |
| WO | WO2002089701 | 11/2002 |

(Continued)

*Primary Examiner* — Sameh Boles
(74) *Attorney, Agent, or Firm* — NuVasive, Inc.

(57) ABSTRACT

A prosthesis for a vertebral column has an upper part (10) for attachment to an upper vertebrae, a lower part (12) for attachment to a lower vertebrae and a middle part (11) located between the upper and the lower parts, wherein the upper part has a lower surface portion with a first radius of curvature, the middle part has an upper surface portion with a second radius of curvature and a lower surface with a third radius of curvature and the lower part has an upper surface with a fourth radius of curvature. The center of the radius of curvature for at least two surfaces is offset rearwardly with respect to a central vertical axis (13) through the upper and lower vertebrae and/or the upper and lower parts. Also defined is device for linking bones, in the form of a band with attachment portions having a number of filaments that provide zones conducive to cellular growth as well as a method of modelling a prosthesis and a process for analyzing performance of a prosthesis.

14 Claims, 30 Drawing Sheets

Related U.S. Application Data continuation of application No. 14/032,143, filed on Sep. 19, 2013, now Pat. No. 9,138,329, which is a continuation of application No. 11/887,984, filed as application No. PCT/AU2006/000457 on Apr. 6, 2006, now abandoned.

(51) Int. Cl.
  *A61F 2/08* (2006.01)
  *A61F 2/30* (2006.01)

(52) U.S. Cl.
  CPC .......... *A61F 2002/3065* (2013.01); *A61F 2002/30654* (2013.01); *A61F 2002/30662* (2013.01); *A61F 2002/30663* (2013.01); *A61F 2002/30884* (2013.01); *A61F 2002/30943* (2013.01); *A61F 2002/443* (2013.01)

(56) References Cited

U.S. PATENT DOCUMENTS

| | | | |
|---|---|---|---|
| 5,401,269 A | 3/1995 | Buttner-Janz et al. | |
| 5,425,773 A | 6/1995 | Boyd | |
| 5,676,701 A | 10/1997 | Yuan | |
| 5,888,226 A | 3/1999 | Rogozinski | |
| 6,368,350 B1 | 4/2002 | Erickson et al. | |
| 6,679,915 B1 | 1/2004 | Cauthern | |
| 6,706,068 B2 | 3/2004 | Ferree | |
| 7,048,764 B2 | 5/2006 | Ferree | |
| 7,503,935 B2 | 3/2009 | Zucherman | |
| 7,887,589 B2 | 2/2011 | Bradley | |
| 2004/0138753 A1 | 7/2004 | Ferree | |
| 2004/0143332 A1* | 7/2004 | Krueger | A61B 17/025 623/17.14 |
| 2004/0199251 A1 | 10/2004 | McCombe et al. | |
| 2004/0243240 A1 | 12/2004 | Beaurain et al. | |
| 2005/0043802 A1 | 2/2005 | Eisermann | |
| 2005/0055098 A1 | 3/2005 | Zdeblick | |
| 2005/0071007 A1 | 3/2005 | Malek | |
| 2005/0131544 A1 | 6/2005 | Kuras et al. | |
| 2005/0149188 A1 | 7/2005 | Cook et al. | |
| 2005/0216092 A1 | 9/2005 | Marik et al. | |
| 2005/0283242 A1 | 12/2005 | Zucherman et al. | |
| 2006/0036325 A1 | 2/2006 | Paul | |
| 2006/0069437 A1 | 3/2006 | Weber | |
| 2006/0095132 A1 | 5/2006 | Kirschman | |
| 2006/0116768 A1 | 6/2006 | Krueger et al. | |
| 2006/0116769 A1 | 6/2006 | Marnay et al. | |
| 2006/0259147 A1 | 11/2006 | Krishna et al. | |
| 2009/0082867 A1 | 5/2009 | Bueno | |

FOREIGN PATENT DOCUMENTS

| | | |
|---|---|---|
| WO | WO2003065929 | 8/2003 |
| WO | WO2004041131 | 5/2004 |
| WO | WO2004098466 | 11/2004 |
| WO | WO2005051243 | 6/2005 |

\* cited by examiner

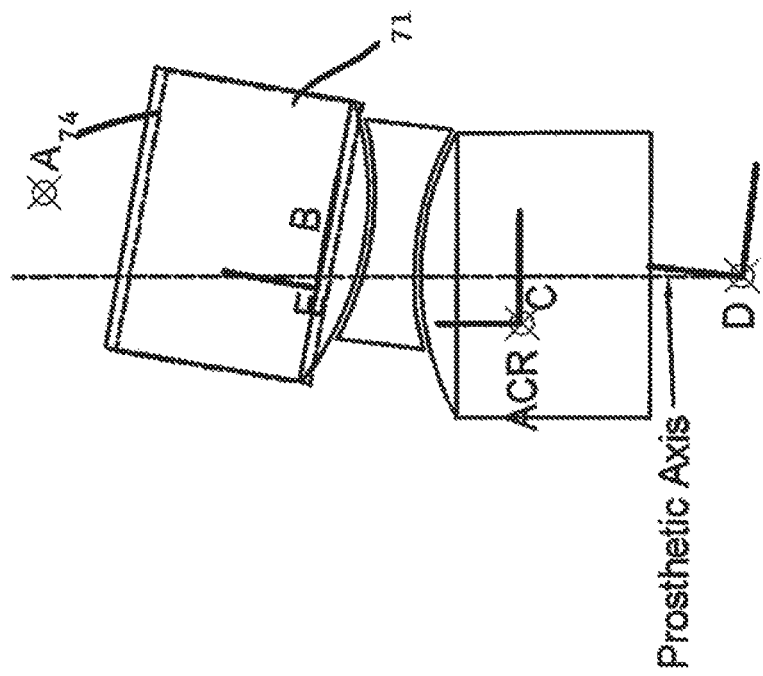
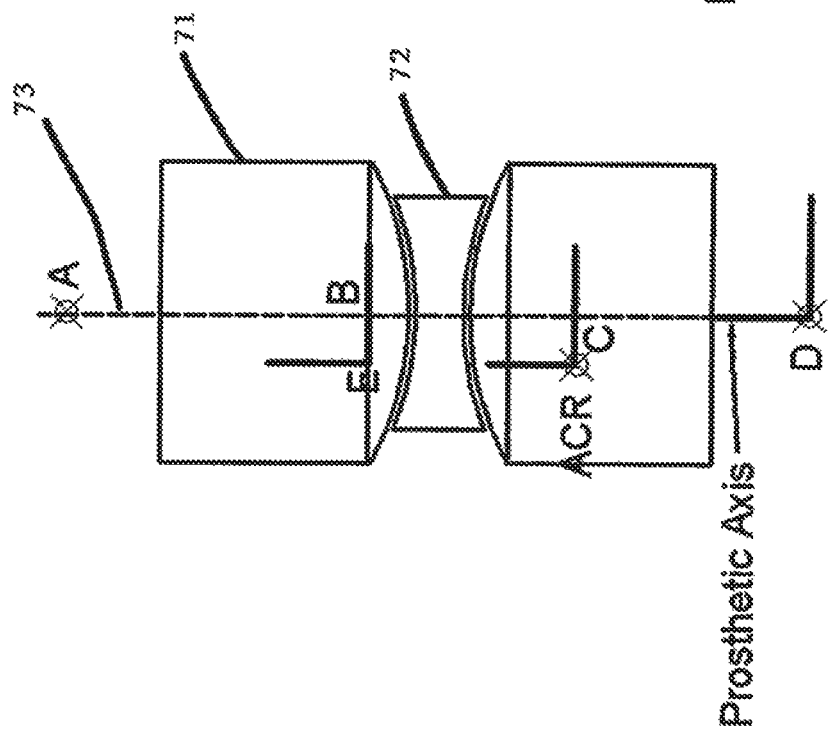

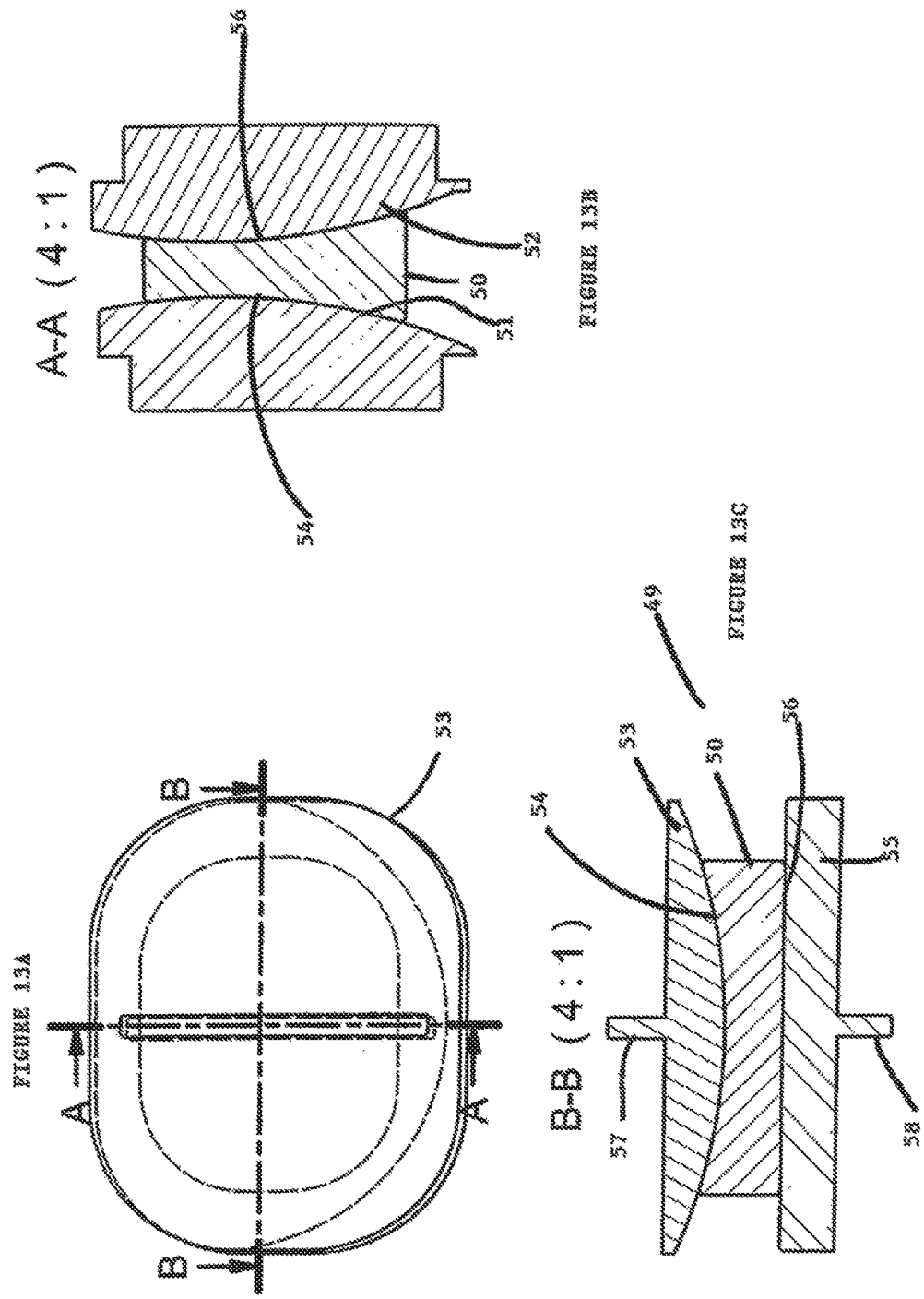

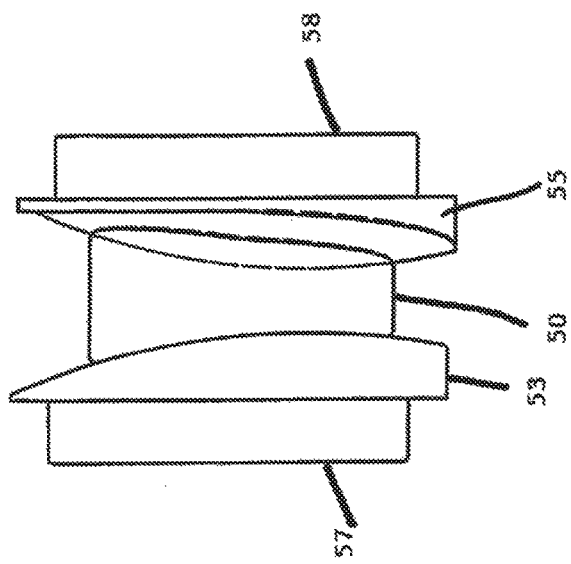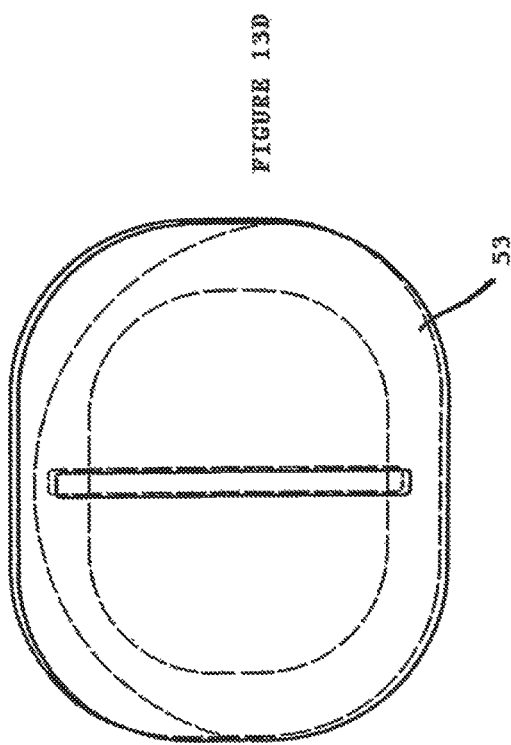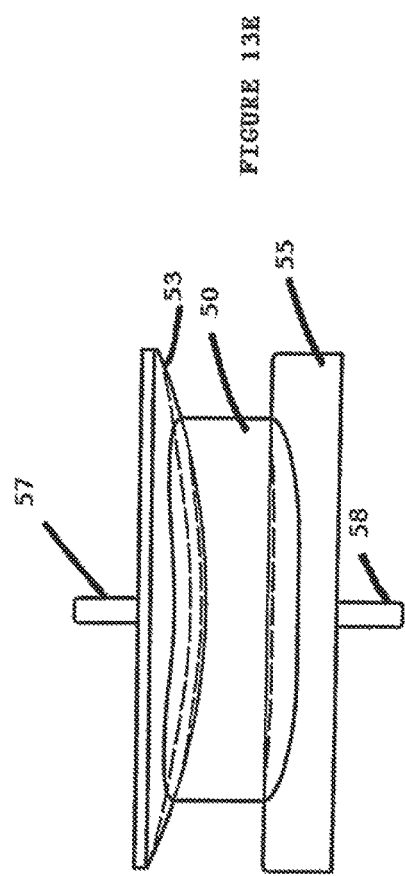

PROSTHESIS

FIELD OF THE INVENTION

The present invention relates to a prosthesis primarily for use as an artificial invertebral disk, predominantly, but not exclusively, for use in human spines.

BACKGROUND OF THE INVENTION

A human invertebral disk maintains a linkage between adjacent vertebrae of the vertebral column. It must fulfil a number of important functions including load bearing and dampening of impact forces. Furthermore, it must permit a complex pattern of movements and resist various stresses, pure or combined, in the sagittal, coronal and axial planes. Assisted by musco-ligamentous structures surrounding the spine, the invertebral disk must also help to maintain the normal alignment of the vertebrae of the spinal column.

An ideal artificial disk replacement will accurately reproduce all the functions of the invertebral disk. However although there have been many different artificial disks which have been described and tested, at this time they have all failed to reproduce the abilities of an invertebral disk.

Typical failings of previous artificial disks have included loosening or dislodgement of vertebral fixation, premature materials wear or structural failure, poor replication of normal or physiological spinal segmental motion and predisposition to the loss of normal neutral vertebral alignment.

An important aspect of the normal motion of the spinal column and the kinematics of the various invertebral motion segments is the behaviour of the motion segments during flexion and extension movements in the sagittal plane. Fundamental to the kinematics is the location of the instantaneous axis of rotation (IAR). The IAR varies from level to level within the spinal column and throughout flexion and extension movements for any given motion segment (level).

One type of spinal disk prosthesis is described in U.S. Pat. No. 5,674,296. The endoprosthesis described consists of a resilient body having a generally elliptical shape. The endoprosthesis is affixed between adjacent upper and lower vertebrae through L-shaped supports each having confronting concave-convex legs for engaging the adjacent bone sectional thickness on one surface and retaining the resilient endoprosthesis therebetween. The endoprosthesis is centrally located between the upper and lower vertebrae to allow central pivoting of the upper vertebrae relative to the lower vertebrae.

In addition to the above a gasket and seal are located at the anterior and posterior regions between the vertebrae to seal the endoprosthesis in its position between the upper and lower vertebrae.

U.S. Pat. No. 5,556,431 describes another type of invertebral disk endoprosthesis in which top and bottom plates are used instead of the L-shaped supports of the above identified US patent. The endoprosthesis described includes a core which has spherical upper and lower surfaces which from drawings shown appear to be aligned with a central vertical axis through the upper and lower vertebrae.

In contrast to U.S. Pat. No. 5,674,296 the prosthesis core of this patent has an edge rim which limits the range of movement of the core and ensures even under extreme conditions cohesion of the prosthesis.

This patent also discloses displacement of the centre of articulation of the prosthesis towards the rear relative to the centre of the vertebral end plates so as to provide sufficient space in the ventral edge area of the prosthesis upper and lower plates so as to enable receipt of bone screws.

Other artificial prostheses have sought to reproduce normal variation in the location of the IAR using various mechanisms including the use of visco-elastic deformable cores. An example of this is shown in U.S. Pat. No. 5,824,094. Unfortunately these type of artificial disks are subject to premature materials wear and stress failure. Furthermore, artificial disks with metallic springs have not yet found their way into clinical use.

All of the artificial disks described above have inherent problems which ultimately create unnatural stresses and resultant pain for an artificial disk implant recipient. The present invention provides an alternative prosthesis which is aimed at mitigating at least some of the problems associated with prior art prosthesis.

SUMMARY OF THE INVENTION

It should be noted that definitions for abbreviations, are provided at the beginning of the details description of the drawings.

According to one embodiment of the present invention there is provided a vertebral disk prosthesis which reproduces substantially similar kinematics of a human invertebral disk.

According to another embodiment of the invention a process for analysing prosthesis performance is provided using a unique modelling method to describe motion of an artificial disk with a mobile core.

According to a further embodiment of the present invention the process of analysis involves a combination of linear algebra and matrix transformations.

It is preferred that the process of analysis enables optimum design of an invertebral disk endoprosthesis.

According to another embodiment of the present invention a prosthesis for a vertebral disk is provided with a mobile core in which the axis of rotation is able to vary, but which can more closely approximate the normal anatomical centre of rotation (ACR) of an existing prosthesis with a mobile core.

According to another embodiment of the invention a disk prosthesis is provided which minimises the adverse effects of abnormal tension in adjacent ligamentis structures.

According to an object of one embodiment of the invention there is provided a disk prosthesis which resists a tendency to adopt an abnormal position or orientation at rest.

It is preferred that a prosthetic disk is provided which has a long life expectancy.

According to one aspect of the present invention there is provided a prosthesis for a vertebral column comprising an upper part for attachment to an upper vertebrae, a lower part for attachment to a lower vertebrae and a middle part located between the upper and lower parts, wherein the upper part has a lower surface portion with a first radius of curvature, the middle part has an upper surface portion with a second radius of curvature and a lower surface portion with a third radius of curvature and the lower part has an upper surface portion with a fourth radius of curvature, wherein the centre of the radius of curvature for at least two surfaces is offset rearwardly with respect to a central vertical axis through the upper and lower vertebrae.

Preferably the centre of the fourth radius of curvature and/or the first radius of curvature is offset rearwardly of the central vertical axis.

It is preferred that the centre of the radius of curvature of all of the surfaces is offset rearwardly with respect to the central vertical axis.

The centre of the radius of curvature for each of the surfaces is preferably located in the posterior third of the prosthesis.

The middle part may have a minor central axis and a major central axis, the minor central axis being located through the centre of the radius of curvature of the second and third surfaces.

The minor central axis may be inclined with respect to the vertical central axis.

It is preferred that the major axis is located through the centre of the posterior and anterior ends of the middle part.

The second and third surfaces may have a substantially similar radius of curvature.

At least one of the second and third surfaces may have one of a convex, concave, cylindrical surface.

The posterior and anterior ends may comprise flat surfaces.

Preferably the middle part has a convex upper surface and a concave lower surface.

Preferably the upper surface of the middle part is concave and the lower surface of the middle part is concave.

Preferably the radius of curvature of the upper surface of the middle part is greater than the radius of curvature of the lower surface.

The flat surfaces may be vertically oriented or slightly skewed in accordance with normal angulation of vertebrae.

It is preferred that the flat surfaces are vertically oriented parallel to the vertical axis plus or minus an angular offset.

According to one embodiment the flat surfaces are parallel to the minor axis.

It is preferred that the centre of the radius of curvature for the third surface is offset rearwardly with respect to the centre of the radius of curvature for the second surface.

The radius of curvature of the third surface according to one embodiment has a centre on a line perpendicular to the major axis.

According to another embodiment the radius of curvature of the third surface has a centre on a line coincident with the minor axis.

According to a further embodiment the radius of curvature of the second surface has a centre on a line at right angles/normal to the major axis.

According to a further embodiment the second surface has a radius of curvature with a centre on a line coincident with the minor axis.

According to a further embodiment the first and fourth surfaces have radii of curvature with a centre similar to that for the third and second surfaces respectively.

It is preferred that the centre of the radius of curvature of the second and/or third surfaces is substantially coincident with a vertical axis through the anatomical centre of rotation.

The length of the second and third surfaces may be substantially the same.

Preferably the length of the end surfaces of the posterior and anterior ends is different.

The posterior end surface may be larger than the anterior end surface if the second and third surfaces are convex.

Preferably if the second and third surfaces are concave then the posterior end surface is smaller than the anterior end surface.

According to one embodiment the second surface has a major portion located forward of the anatomical centre of rotation.

The third surface may have a major portion located forward of the anatomical centre of rotation.

It is preferred that each of the surfaces have a major portion located forward of the anatomical centre of rotation and the minor portion located rearwardly of it.

The middle part may be asymmetric.

Preferably a major portion of the middle part is located forward of the anatomical centre of rotation when the upper and lower vertebrae are substantially vertically aligned.

According to one embodiment the minor axis of the middle part when in a vertical orientation close to its point of rest (equilibrium with the upper and lower vertebrae) is as close as possible if not coincident with a vertical axis through the anatomical centre of rotation.

The upper part may comprise an axis of symmetry which is offset to the posterior end.

The axis of symmetry may coincide with the centre of radius of curvature of the first surface.

The axis of symmetry preferably passes through the anatomical centre of rotation.

The lower part may comprise an axis of symmetry which passes through the anatomical centre of rotation.

Preferably the first and second surfaces have substantially matching radii of curvature.

Preferably the third and fourth surfaces have substantially matching radii of curvature.

The upper part may comprise an anterior portion which is larger than a posterior portion relative to the axis of symmetry.

The lower part may comprise an anterior portion which is larger than a posterior portion relative to the axis of symmetry.

It is preferred that the middle part is movable relative to the upper and lower parts.

Movement of the middle part is preferably limited by stopping means located behind and in front of the middle part.

The stopping means may include end portions of the upper and lower parts.

The upper and lower parts may be fixed to the upper and lower vertebrae and configured to form a small gap between respective anterior end portions and a larger gap between respective posterior end portions.

Preferably the second and/or third surfaces include a curved surface portion.

The curved surface portion preferably has a substantially spherical profile with a radius of curvature.

It is preferred that the second and third surfaces have centres of radius of curvature which are vertically offset.

Preferably the first and second surfaces have substantially similar radii of curvature of opposite sign.

The third and fourth surfaces may have substantially similar radii of curvature of opposite sine.

According to one embodiment the second radius of curvature is different than the third radius of curvature.

According to an alternative embodiment the third radius of curvature is greater than the first or less than the first.

The third surface may be offset more than the second from the central vertical axis of the vertebrae.

It is preferred according to one embodiment that the parts of the prosthesis are designed asymmetrically to correspond to the asymmetry of upper and lower vertebrae with which they are to be used.

It is to be understood that any of the embodiments or preferred options described previously include variations in which all surfaces are tilted or skewed.

It is preferred that the lower part and upper part include a stop surface at a rearward part to limit rearward movement of the middle part.

The length of one of the second/third surfaces may be greater than the other when measured front to back. The fourth surface preferably includes a flat forward portion extending from a front end of a curved portion.

The curved portion preferably has a spherical cylindrical profile.

It is preferred that the top and bottom surfaces are convex.

According to another aspect of the present invention there is provided a device for linking bones comprising a band having first and second ends each with attachment portions for attachment to upper and lower bones and a plurality of filaments configured to provide a plurality of zones conducive to cellular growth.

It is preferred that the plurality of zones comprise spaces.

The plurality of filaments may be configured to form a matrix.

According to one embodiment the plurality of zones comprise a plurality of interwoven portions.

The filaments may be woven together.

The band preferably comprises a gauze or mesh.

The band may have inherent stiffness.

Preferably the band is resiliently deformable.

It is preferred that the band is extendible and compressible.

The zones may comprise spaces between filaments.

The zones according to one embodiment include overlapping regions of filaments.

Preferably the spaces are formed by filaments.

According to another embodiment the filaments are configured in parallel and perpendicular rows forming an intersecting grid pattern.

It is preferred that the device is used for linking upper and lower vertebrae.

It is preferred that the band is connected to an anterior portion of upper and lower vertebrae.

The band may be generally flat.

The band may be in the form of a flat strap.

The band may be composed of fabric, metal or a polymeric substance.

It is preferred that the band is made from a substance which dissolves in use.

The band preferably can concertina or lozenge.

According to one embodiment the band provides axial support against a predetermined level of compression.

According to a further embodiment the band provides a predetermined level of resilient extension.

Each attachment portion may comprise a plate or strap with holes to allow fixing elements to be inserted therethrough.

According to another aspect of the present invention there is provided a prosthesis for vertebrae having one or more of the features of the previously described prosthesis wherein the upper part when the prosthesis is attached to upper and lower vertebrae, closely simulates rotational and translational movements possible with an invertebral disk.

According to another aspect of the present invention there is provided a method of producing a prosthesis for vertebrae comprising providing a model for designing a prosthesis used to simulate kinematics of an invertebral disk, using the model to produce a prosthesis comprising an upper part, a lower part and a middle part, which prosthesis simulates kinematics of an invertebral disk and wherein the upper part when the prosthesis is attached to upper and lower vertebrae simulates rotational and translational movements possible with an invertebral disk.

Preferably the simulation provided by the prosthesis includes tilting of the upper part relative to the anatomical centre of rotation of the lower vertebral disk.

The simulation provided by the prosthesis may include movement during rotation along an arc permissible with an invertebral disk.

The simulation provided by the prosthesis may include translational movement forward and back to an extent permissible for an upper vertebrae with an invertebral disk.

It is to be noted that the anatomical centre of rotation may vary for adjacent pairs of upper and lower vertebrae in a vertebral column.

According to one embodiment the radius of curvature for the first and second surfaces is selected based on rotational movement possible for an upper vertebrae with respect to a lower vertebrae.

According to another embodiment the third and fourth surfaces have a radius of curvature which is selected to simulate the amount of tilting possible for the upper vertebrae.

It is preferred that the angle of tilting permissible for the upper vertebrae and the angle indicative of the rotational movement of the upper vertebrae together closely approximate the angular displacement of an upper vertebrae with respect to a lower vertebrae with an invertebral disk between the upper and lower vertebrae.

According to another aspect of the present invention there is provided a process for analysing performance of a prosthesis for use between upper and lower vertebrae, the process comprising determining a first centre of radius of curvature for a lower surface of a middle part of a prosthesis, determining a second centre of radius of curvature for an upper surface of the middle part of the prosthesis, providing a link between the first centre of radius of curvature and second centre of radius of curvature, rotating the second centre of radius of curvature with respect to the first centre of radius of curvature by $\alpha$ degrees representing tilting of the upper vertebrae, rotating a portion of the first link by $\beta$ degrees whereby the length of the portion corresponds to the length from the second centre of rotation of curvature to the centre of the lower surface of the upper vertebrae or upper surface of the upper part whereby $\beta$ corresponds to angular movement of the upper part over the upper surface of the middle part, determining the anatomical centre of rotation, determining an angle $\gamma$ corresponding to the desired angle of rotation of an invertebral disk relative to the anatomical centre of rotation, comparing the angle $\gamma$ with the angles $\alpha+\beta$ and designing a prosthesis with values for the upper and lower centre of radius of curvature which minimises the value of $\gamma-(\alpha+\beta)$.

According to a further aspect of the present invention there is provided a process similar to the process described above except that the first two determining steps are replaced by the steps of determining an upper centre of radius of curvature for an upper surface of a lower part of a prosthesis and determining a lower centre of radius of curvature for a lower surface of an upper part of the prosthesis.

According to one embodiment the link passes through the minor axis of the middle part.

According to another embodiment the angle $\alpha$ corresponds to the angle between the upper centre of radius of curvature relative to a central vertical axis of the upper and lower vertebrae (prosthesis axis).

According to one embodiment the angle β corresponds to the angle formed by moving the first link through an angle whereby the link coincides with a central point on the lower surface of the upper vertebrae when moved a maximum permissible amount relative to the anatomical centre of rotation.

According to different embodiments of the present invention the second and third surfaces may be any one of the following combinations:
convex/convex;
concave/concave;
concave/convex;
convex/concave;
convex/cylindrical;
concave/cylindrical.

It is preferred that the process includes determining the length of the first link and the length of a second link between the lower centre of radius of curvature and the centre point on the lower surface of the upper vertebrae.

According to a further embodiment of the present invention the method involves converting a frame located at the anatomical centre of rotation to a global co-ordinate system and moving the frame by translational and rotational transformations to relocate the frame at either the centre of the lower surface of the upper vertebrae or a point on the lower surface of the upper vertebrae that lies on a vertical axis through the anatomical centre of rotation when the upper vertebrae is in rest above the lower vertebrae.

It is preferred that the transformations involved include the algebraic and matrix transformations described in the preferred embodiment.

According to one embodiment the process involves designing the prosthesis so that the maximal change in ligament length due to prosthesis malplacement is minimised. Prosthesis malplacement can be defined by the value of the horizontal distance between the prosthesis axis and the patients centre of rotation (value Ldsk in FIG. 5*a*, 5*c* and value L in FIGS. 19A and 19B).

According to another embodiment the process involves designing a mechanism such that the ligament is stretched in such a way as to be under more tension in flexion and extension and be under the least tension in the neutral position. Such a mechanism will provide a restoring force that will tend to move the prosthesis back to a neutral position.

According to a further aspect of the present invention there is provided a modelling method for a prosthesis comprising:

determining a frame matrix FR1 in at least 2D for a prosthesis in situ between upper and lower vertebrae representing a co-ordinate system for a reference point at the ACE of a linear vertebrae.

determining a reference frame B1 for a point at the CUPR expressed in terms relative to the frame FR1 at the ACR;

$$\text{where } B1 = \begin{bmatrix} 1 & 0 & l \\ 0 & 1 & p \\ 0 & 0 & 1 \end{bmatrix}$$

where
l=the distance of the CUPR from the ACR along an x axis; or
p=the distance of the CUPR from the ACR along a y axis, Rotating the frame B1 by α° to produce a new frame B2=B1×T where α is the angle of rotation of the CLPR in relation to the CUPR; and T is a transformation matrix:

$$\begin{bmatrix} \cos\alpha & -\sin\alpha & \Delta x \\ \sin\alpha & \cos\alpha & \Delta y \\ 0 & 0 & 1 \end{bmatrix}$$

translating the frame B2 by the distance b of the CUPR to the CLPR along the y-axes to produce a frame B3:
where the translation matrix $$= \begin{bmatrix} 1 & 0 & 0 \\ 0 & 1 & -b \\ 0 & 0 & 1 \end{bmatrix}$$

rotating the frame B3 by β degrees using T to produce a new frame
B4=B3×T
where β is the angle of rotation of a point B on an upper vertebrae relative to the CLPR, translating the frame B4 by the distance C of the CLPR to point B along the y axes to produce a new frame B5.

$$\text{where } B5 \begin{bmatrix} 1 & 0 & 0 \\ 0 & 1 & C \\ 0 & 0 & 1 \end{bmatrix}$$

translating the frame B5 by the distance 1 of the point B along the x-axis to a point E co-axial with a vertical axis through the ACR, to produce a new frame B6
where the translation matrix is $$\begin{bmatrix} 1 & 0 & l \\ 0 & 1 & 0 \\ 0 & 0 & 1 \end{bmatrix}$$

rotating frame A1 by γ using T to produce a new frame A2.
γ=normal rotation of an upper vertebrae relating to the ACR.

Translating A2 by a distance h of the ACR to point E along the y-axis to produce a frame A3 where the translation matrix is $$\begin{bmatrix} 1 & 0 & 0 \\ 0 & 1 & h \\ 0 & 0 & 1 \end{bmatrix}$$

Comparing B6 and A3 to determine how clearly the prosthesis simulates kinematics of an invertebral disk.

According to one embodiment frames B6 and A3 are rotated by γ° about global reference frame A1 to produce new frames A4 and B7.

Preferably the step of comparing includes solving at least one of the following equations for a minimum value.

$$A3(1,3)-B6(1,3)=0A4(1,3)-B7(1,3)-0$$

$A3(2,3)-B6(2,3)=0$ or $A4(2,3)-B7(2,3)=0$ where the numbers in brackets represent rows and columns respectively of the applicable matrix.

According to another embodiment the step of comparing includes solving simultaneous equations for equivalent rows and columns of A4 and B7.

It is preferred that reference frame A1 is a global reference frame.

It is to be understood that use of the word simulation is intended to be interpreted broadly to cover similar and not just exact reproductions.

The word "prosthesis" is intended to cover any artificial insert having any number of components.

The modelling method used for analysing performance of a prosthesis preferably describes motion of an artificial disk that has a mobile core and is constrained by adjacent ligamentous structures.

The modelling method preferably can be used to optimise the various design parameters of a mobile core prosthesis so as to more accurately reproduce the location of the IAR of a normal disk and minimise the tendency to follow or adopt an abnormal path of motion during flexion/extension movements and/or an abnormal neutral alignment in the sagittal plane at rest.

Using the modelling method it can be shown that for a prosthesis with a mobile core possessing upper and lower plates with articulating surfaces, according to a preferred embodiment of the present invention the following applies:

1. The larger the radius, the more the core will need to translate for a given change in orientation.
2. The smaller the radius, the less the core will need to translate for a given change in orientation.
3. For a given change in position and orientation;
   (a) The closer the axis of rotation of the prosthesis is to the normal anatomical centre of rotation, the less the LLS need to change length.
   (c) The more the radii of the upper and lower articulating surfaces of a bi-convex or bi-concave prosthesis are unequal, the more the LLS need to stretch, if the axis of rotation of the prosthesis is displaced anterior to the anatomical centre of rotation.
   (d) If the axis of rotation of the disc prosthesis is displaced anterior to the normal anatomical axis of rotation, during flexion, the final position and orientation of the upper vertebra will be determined by the ability of both the PLL and the LLS to stretch. It follows that there four possibilities:
      (i) PLL can't stretch & LLS can't stretch—the upper vertebra cannot move,
      (ii) PLL can stretch & LLS can't stretch—the upper vertebra will adopt a position of kyphosis,
      (iii) PLL can stretch and LLS can stretch—the upper vertebra will be unstable and may adopt a non-anatomical position/orientation
      (iv) PLL can't stretch and LLS can stretch—unlikely to occur in clinical practice
   It follows that for the upper vertebra to adopt a given orientation during flexion, the LLS must stretch and therefore the final vertebral position will not be normal.
   (e) If the axis of rotation of the disc prosthesis is displaced anterior to the normal anatomical axis of rotation, during extension, the final position and orientation of the upper vertebra will be entirely determined by the ability of the LLS to stretch. This is because the ALL has been resected during the surgical approach. It follows that there are two possibilities:
      i) The LLS can't stretch—the upper vertebra will adopt a position of less lordosis than normal,
      (ii) The LLS can stretch—the upper vertebra can adopt the normal orientation but will have an abnormal position which is permitted by stretch of the LLS.
4. Movement of the prosthesis axis of rotation close to the normal ACR will:
   (i) Minimize the need for the ligaments to stretch or shorten during normal flexion and extension movements
   (ii) Optimize the ability of the vertebra to adopt normal orientation and position during flexion and extension movements
5. Movement of the prosthesis axis towards the normal anatomical position for the ACR lying below the posterior half of the disc space introduces two new problems;
   (i) Posterior translation of the core on flexion, with an existing bi-convex design, causing neural compression. A solution is to use a bi-concave core. A bi-concave core mechanism will cause the core to move anteriorly with flexion and posteriorly with extension.
   (ii) In some embodiments the core becomes asymmetrical around the prosthetic axis. Rotation around this axis would therefore produce neural compression. One solution to prevent rotation around the prosthetic axis is by making one of the two prosthetic articulations cylindrical rather than spherical. A further solution is to make one of the two prosthetic articulations an ellipsoid shape. Yet another solution is to have both surfaces spherical but placing mechanical stops or guide fins.
6. In another embodiment, the Mathematical Process can be used to optimize a disc mechanism consisting of curved upper and lower articulations where the arc centres are below the disc base but where the radii are unequal. This may permit variation in the vertical location of the prosthesis axis of rotation but restrict it to below the disc base. Such a prosthesis would not have the ability to achieve certain undesirable positions that would be readily apparent to someone skilled in the art.
7. It follows that following resection of the anatomical ALL for anterior insertion of an internally unconstrained disc prosthesis, that the prosthesis may not function correctly without appropriate tension in the adjacent ligamentous structures. The placement of constraints within the disc prosthesis will strain the prosthesis/vertebral interface and may predispose to loosening of the prosthesis. However under some circumstances it may be desirable to allow the placement of material that is attached to the lower non articulating surface of the upper part and to the upper non articulating surface of the lower part. Such material could be made out of any appropriate elastic material (such as, but not restricted to, a polymer) that could increase the stiffness of the construct in a desirable way. While the Mathematical Process may be used to design a prosthesis which will minimize the effect of abnormal tension in the adjacent ligamentous structures, the prosthesis may optimally be further supported by the placement of an artificial ALL, attached to anterior aspect of the vertebral bodies and separate from the disc prosthesis.

It is preferred that following resection of the anatomical LLL for anterior insertion of an internally unconstrained disk prosthesis, that the prosthesis may not function correctly without appropriate tension in the adjacent ligamentous structures. The placement of constraints within the disk prosthesis will strain the prosthesis/vertebral interface and may predispose to loosening of the prosthesis. While the mathematical process may be used to design a prosthesis which will minimise the effect of abnormal tension in the adjacent ligamentous structures, the prosthesis may optimally be further supported by the placement of an artificial ALL, attached to anterior aspect of the vertebral bodies and separate from the disk prosthesis.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

BRIEF DESCRIPTION OF THE DRAWINGS

Preferred embodiments of the present invention will now be described by way of example only with reference to the accompanying drawings in which:

FIG. 10A shows a prosthesis according to another embodiment with upper and lower vertebrae in rest positions;

FIG. 10B shows the prosthesis shown in FIG. 10A with the upper vertebrae rotated by 10°;

FIG. 13A shows a top view of a prosthesis according to another embodiment of the present invention;

FIG. 13B shows a cross-sectional view of the prosthesis of FIG. 13A taken along sectional lines A-A;

FIG. 13C shows a cross-sectional view of the prosthesis shown in FIG. 13A taken along sectional lines B-B;

FIG. 13D shows a top view of the prosthesis shown in FIG. 13A;

FIG. 13E shows a rear view of the prosthesis shown in FIG. 13A;

FIG. 13F shows a side view of the prosthesis shown in FIG. 13A with the left hand side representing the posterior end;

DETAILED DESCRIPTION OF THE DRAWINGS

To assist with an understanding of the invention terminology used is set out below.

Figure 1:
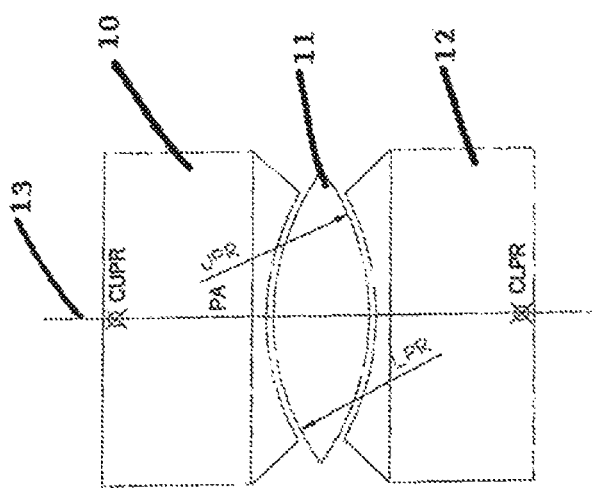
FIG. 1 shows a schematic diagram of a prior art prosthesis between upper and lower vertebrae.

Terminology a. Centre of Rotation (COR): A point around which an object is rotated to achieved a desired position and orientation with zero translation. (Translation is defined as a pure linear movement in any direction without change in orientation).

b. Instantaneous Axis of Rotation (IAR): The location of the COR at any instant in time as it varies in exact location during the course of movement (such as flexion and extension) between two end points.

c. Anatomical Centre of Rotation (ACR): The centre of rotation of an undiseased cervical motion segment between two end points (such as flexion and extension).

d. Upper and lower Prosthesis Radii (UPR & LPR): The upper and lower radii of curvature of the disc prosthesis, e. Centre of Upper and Lower Prosthesis Radii (CUPR & CLPR): The centre point of the upper and lower disc prosthesis radii. For a bi-convex disc prosthesis core, the CUPR lies inferior and the CLPR lies superior.
f. Prosthetic axis (PA): The line joining the CUPR and LUPR.
g. Lateral ligament structure (LLS): The ligaments taking origin from the supero-lateral edge of the lower vertebra and attached to the infero-lateral edge of the upper vertebra, along lines radiating upwards and forwards from the ACR and which stretch the least during vertebral segmental flexion and extension around the ACR.
h. Simplified lateral ligament structure (SLLS): A single line or intervertebral linkage which describes the mathematical behaviour of the LLS.
i. Anterior longitudinal ligament (ALL): The anterior ligamentous structures.
j. Posterior longitudinal ligament (PLL): The posterior ligamentous structures.
k. The Mathematical Process: A mathematical process involving linear algebra and matrix transformations which can be used to describe the motion of an artificial disc that has a mobile core FIG. 1 shows a prosthesis with a bi-convex core representing a prior art prosthesis as shown for example in U.S. Pat. No. 5,674,296 to Bryan.

From FIG. 1 it should be apparent that the upper vertebrae 10 can rotate relative to the core 11 and the core 11 can rotate relative to the lower vertebrae 12.

It has been assumed in the past that because there is in effect two angles of rotation, that the prosthesis can adopt whatever position is needed to simulate normal rotation. However an analysis in accordance with a preferred embodiment of the invention shows that exact simulation of normal rotation is not possible but it is possible to design a prosthesis with near normal motion.

Incremental normal rotation in the sagittal plane occurs around an instantaneous centre of rotation. When measured over larger angles this ICR moves somewhat, although in both the lumber and cervical spines it is always in the posterior one half of the lower vertebrae.

Figure 2:
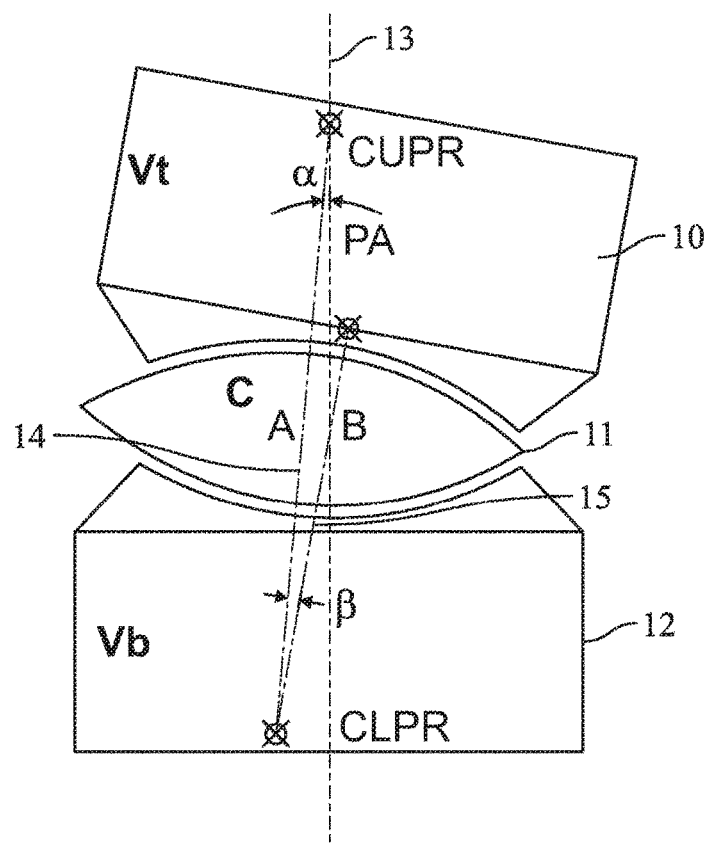
FIG. 2 shows a dual linkage model of a prosthesis in accordance with an embodiment of the present invention.

In accordance with one embodiment of the invention, motion of the upper vertebrae 10 can be described by analysing it as a dual linkage with links 14 and 15 as shown in FIG. 2. Point CUPR remains fixed in global co-ordinates. The motion can be considered as sequential movements of the links 14 and 15. Initially upper vertebrae 10, the core 11 and the point CLPR rotate by a degrees around the point CUPR. The lower vertebrae 12 then rotate by β degrees around the newly rotated position of CLPR (CLPR$^1$).

The minor axis (not shown) of the core 11 remains at right angles to link A which itself passes through the minor axis of the core 11. Core 11 therefore moves in the same direction to upper vertebrae 10. In flexion core 11 will anteriorly, in extension core 11 will move posteriorly.

In designing a prosthesis as previously outlined it is desirable to simulate as closely as possible movement of vertebrae in normal operation with an invertebral disk between upper and lower vertebrae. Therefore to provide a frame of reference of this normal motion reference is made to FIG. 3 which shows motion of a normal disk, (invertebral disk) with the approximation of a fixed centre of rotation (ACR). All points on vertebrae 10 move to corresponding points on vertebrae 18 and the transformation that describes the movement of any arbitrary point from the position of upper vertebrae 10 to upper vertebrae 16 is rotation by angle γ around ACR. Lines 17 and 18 both exhibit positional information and angular information. These characteristics are defined as position and orientation.

Figure 3:
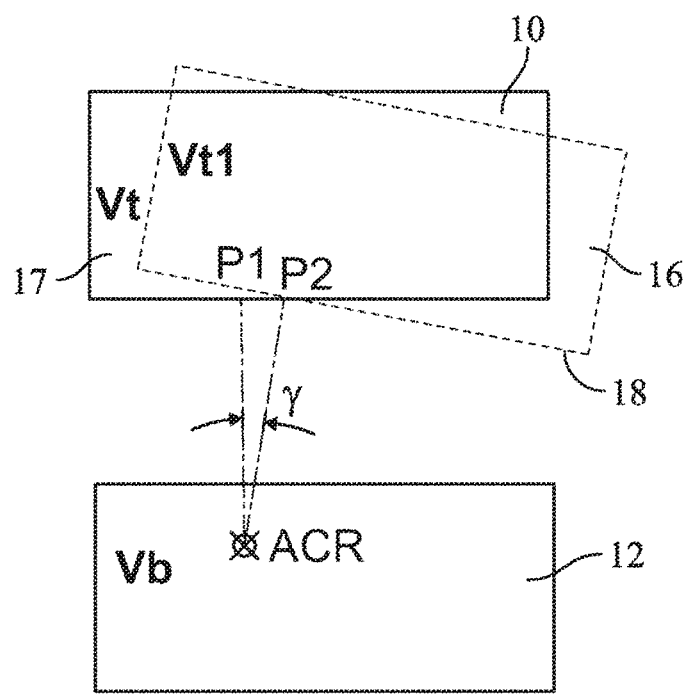
FIG. 3 shows a schematic of motion of a normal invertebral disk about an anatomical centre of rotation.

It follows that for any artificial disk mechanism to reproduce the behaviour of the movement shown in FIG. 3 that it must be able to move line segment 17 to line segment 18 and at the end of the movement both the position and orientation of line segment C1-D1 with the artificial disk mechanism (prosthesis) must match the line segment 18 in FIG. 3.

Referring back to FIG. 2 it follows that the position and orientation of the vertebrae are fully described by angles α and β and the lengths of the links 14 and 15. It follows that if the mechanism in FIG. 2 is able to mimic the mechanism in FIG. 3 (normal) then there must exist a combination of values for variables α, β, 14, 15 that will make both the position and orientation of both vertebrae the same.

Figure 4:
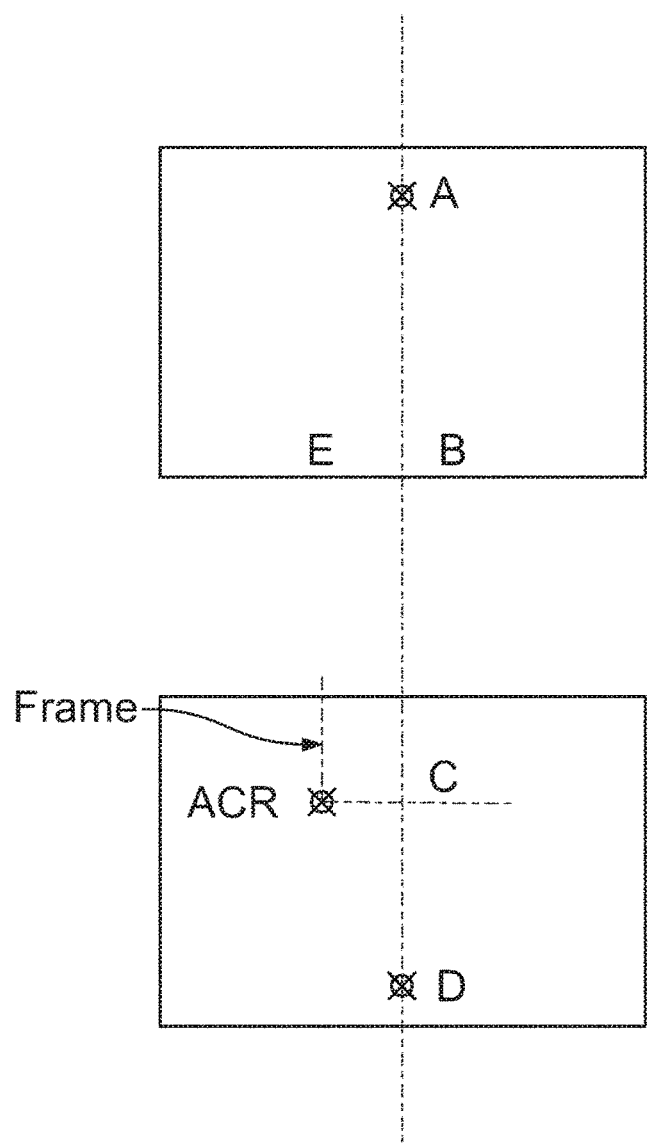
FIG. 4 shows a schematic diagram of upper and lower vertebrae with attached global reference frame in accordance with a preferred embodiment of the present invention.

Position and orientation of objects in two dimensional space are conveniently describe by the use of linear algebra. To fully describe the position and orientation of a two dimensional structure in two dimensional space, a coordinate system can be attached to the object. This coordinate system is called a frame. All points on the moving object have fixed coordinates in the new frame and the frame is considered to move within another coordinate system—usually the global or 'world' coordinate system. FIG. 4 shows a Frame FR1 attached to the moving vertebrae in FIG. 3. The origin of this frame is displaced from the origin of the global frame G by position vector p. The orientation of frame FR1 is given by the unit vectors n for the x axis and o for the y axis of FR1.

In matrix notation the frame FR1 can be described as $$FR1 = \begin{bmatrix} \bar{n}_x & \bar{o}_x & \bar{p}_x \\ \bar{n}_y & \bar{o}_y & \bar{p}_y \\ 0 & 0 & 1 \end{bmatrix}$$

Where $\bar{n}_x$=x coordinate of unit vector $\bar{n}$
$\bar{n}_y$=y coordinate of unit vector $\bar{n}$
$\bar{o}_x$=x coordinate of unit vector $\bar{o}$
$\bar{o}_y$=y coordinate of unit vector $\bar{o}$
$\bar{p}_x$=x coordinate of position vector $\bar{p}$
$\bar{p}_y$=y coordinate of position vector $\bar{p}$ Any point with coordinates x,y attached to frame FR1 can be converted to global coordinates by premultiplying matrix FR1 by the vector of the coordinates of the point in FR1

$$FR1 * \begin{bmatrix} x \\ y \\ 1 \end{bmatrix} = \begin{bmatrix} x_{global} \\ y_{global} \\ 1 \end{bmatrix}$$

Any frame such as FR1 can be transformed by multiplying by a transformation matrix T with the following characteristics.

$$T = \begin{bmatrix} \cos\alpha & -\sin\alpha & \Delta x \\ \sin\alpha & \cos\alpha & \Delta y \\ 0 & 0 & 1 \end{bmatrix}$$

Where α=angle of rotation
Δx and Δy=change in x and y position.

If matrix M is premultiplied by Frame FR1 frame FR1 will be rotated around the fixed global reference frame origin and translated in the direction of the global reference frames axes. If Matrix M is postmultilpied by FR1, FR1 is rotated around the origin of the moving frame (FR1) and translated in the direction of the moving (FR1) frames axes.

FIGS. 5A to 5D show a hypothetical prosthesis with a convex upper surface and a concave lower surface. For analysis purposes there is a mechanical linkage consisting of line segment AD rotating around point A and a further link consisting of line segment DB, DB is rigidly attached to the upper vertebrae and upper prosthetic end plate. A reference frame has been attached at point ACR. A further reference frame has been attached at point A.

Figure 5A:
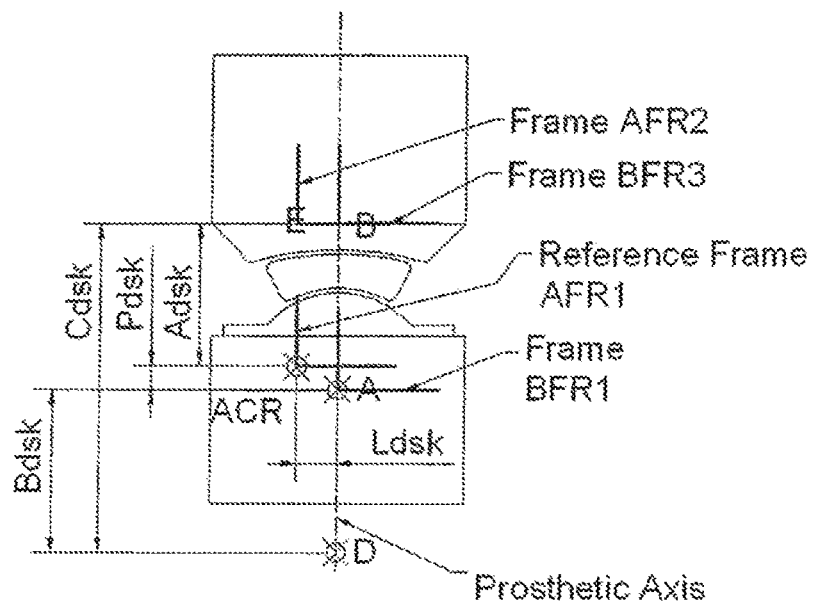
FIGS. 5A and 5C show a schematic diagram of a prosthesis (convex/concave and bi-concave core respectively) and upper and lower vertebrae showing translational characteristics of a model according to the preferred embodiment of the invention.
Figure 5B:
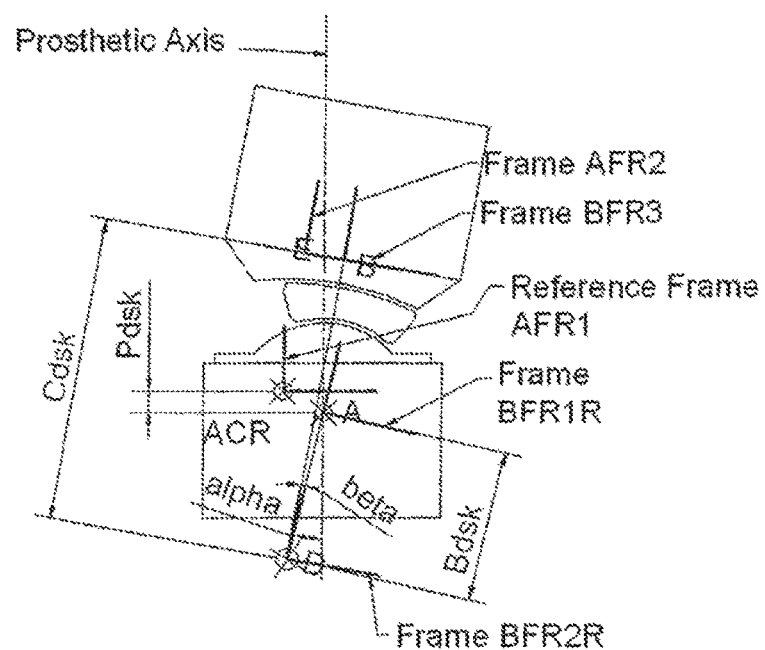
FIGS. 5B and 5D show rotational characteristics of the model shown in FIGS. 5A and 5C.
Figure 5C:
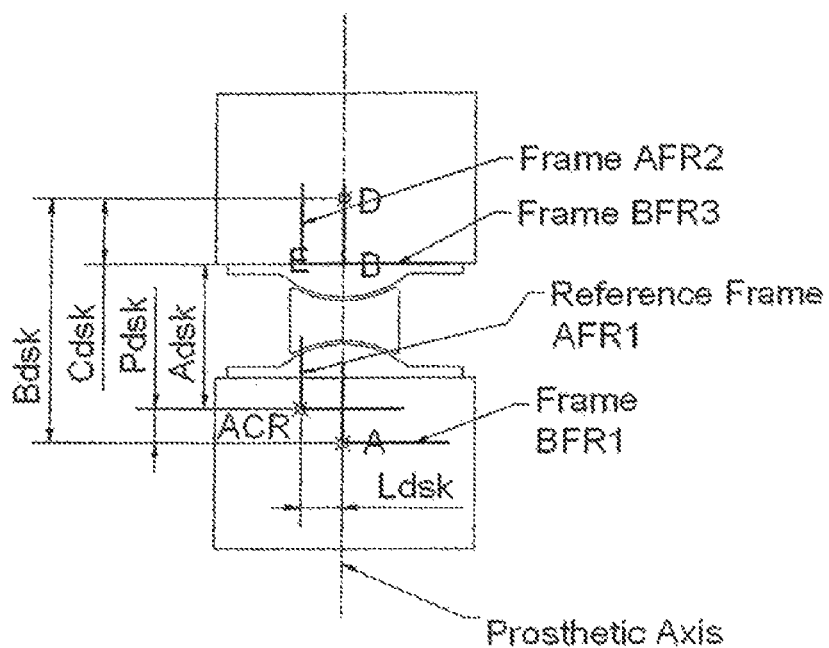

Considering the variables in FIGS. 5A and 5C it should be apparent that BFR1 should have the following value—expressed in the global reference frame AFR1.

$$BFR1 = \begin{bmatrix} 1 & 0 & Ldsk \\ 0 & 1 & Pdsk \\ 0 & 0 & 1 \end{bmatrix}$$

Figure 5D:
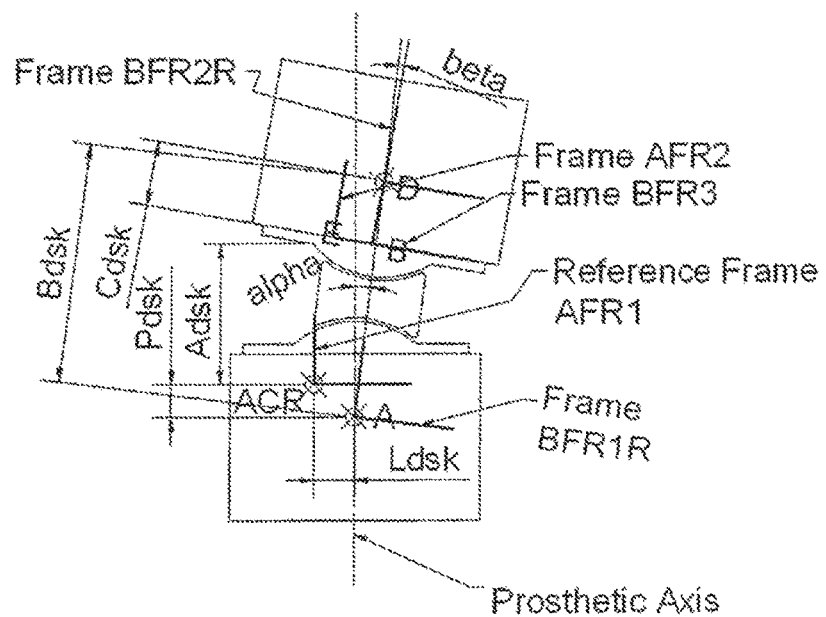

In order for the reference frame BFR1 to be transformed to be attached to the top vertebrae at point B, it must undergo the following transformations shown in FIGS. 5B and 5D.

1. Rotation by alpha degrees to produce new frame BFR1R $$BFR1R = BFR1 * \begin{bmatrix} \cos\alpha & -\sin\alpha & 0 \\ \sin\alpha & \cos\alpha & 0 \\ 0 & 0 & 1 \end{bmatrix}$$

in FIG. 1 alpha is negative considering the normal convention of positive rotation being anticlockwise.

2. Inferior translation by Bdsk in the frame of reference of BFR1R to produce new frame BFR2

$$BFR2 = BFR1R * \begin{bmatrix} 1 & 0 & 0 \\ 0 & 1 & -Bdsk \\ 0 & 0 & 1 \end{bmatrix}$$

3. Rotation of BFR2 by Beta degrees in its own frame of reference to produce new frame BFR2R $$BFR2R = BFR2 * \begin{bmatrix} \cos\beta & -\sin\beta & 0 \\ \sin\beta & \cos\beta & 0 \\ 0 & 0 & 1 \end{bmatrix}$$

4. Translation by Cdsk in the frame of reference BFR2R to produce a new frame BFR3

$$BFR3 = BFR2R * \begin{bmatrix} 1 & 0 & 0 \\ 0 & 1 & Cdsk \\ 0 & 0 & 1 \end{bmatrix}$$

BFR3 is now attached to the upper vertebrae at point B and has the orientation of the upper vertebrae. BFR3(1,3) (row 1, column 3) contains a function & (alpha,Beta) that represents the x coordinate of point B and BFR3(2,3) contains a function g(alpha, Beta) that represents the y coordinate of point B. BFR3(1,1) contains a function k (alpha,Beta) that represents the cosine of the angle made by the top vertebrae with the global reference frame.

Consider a further linear translation of −Ldsk in the frame of reference of BFR3 (the upper vertebrae. This will create at new frame BFR4 at point E $$BFR4 = BFR3 * \begin{bmatrix} 1 & 0 & -Ldsk \\ 0 & 1 & 0 \\ 0 & 0 & 1 \end{bmatrix}$$

The equivalent functions f, g and k now represent the coordinates of point E and the (unchanged) angle of orientation of the upper vertebrae.

By performing the matrix calculations It can be shown that $$f(\alpha/\beta)=-(\cos\alpha\cdot\cos\beta-\sin\alpha\cdot\sin\beta)\cdot Ldsk+(-\cos\alpha\cdot\sin\beta-\sin\alpha\cdot\cos\beta)\cdot Cdsk+\sin\alpha\cdot Bdsk+Ldsk) \quad (1)$$

Where f=x coordinate of point E $$g(\alpha/\beta)=-(\sin\alpha\cdot\cos\beta-\cos\alpha\cdot\sin\beta)\cdot Ldsk+(-\cos\alpha\cdot\sin\beta-\sin\alpha\cdot\sin\beta)\cdot Cdsk+\cos\alpha\cdot Bdsk+Pdsk) \quad (2)$$

Where g=y coordinate of point E
And $$k(\alpha,\beta)=\cos\alpha\cdot\cos\beta\sin\alpha\cdot\sin\beta \quad (3)$$

Where k=cosine of angle between upper vertebrae and global reference frame.

From FIG. 5 it can be seen that as AFR1 is the global reference frame it's value is $$AFR1 = \begin{bmatrix} 1 & 0 & 0 \\ 0 & 1 & 0 \\ 0 & 0 & 1 \end{bmatrix}$$

a frame AFR2 can be derived by rotation by angle gamma (the desired rotation of the normal disc) of frame AFR1 to produce AFR1R $$AFR1R = AFR1 * \begin{bmatrix} \cos\gamma & -\sin\gamma & 0 \\ \sin\gamma & \cos\gamma & 0 \\ 0 & 0 & 1 \end{bmatrix}$$

Frame AFR1R can now be translated by value Adsk along the y axis of AFR1R to produce frame AFR2

$$AFR2 = AFR1R * \begin{bmatrix} 1 & 0 & 0 \\ 0 & 1 & Adsk \\ 0 & 0 & 1 \end{bmatrix}$$

$$AFR2 = \begin{bmatrix} \cos\gamma & -\sin\gamma & -\sin\gamma\cdot Adsk \\ \sin\gamma & \cos\gamma & \cos\gamma\cdot Adsk \\ 0 & 0 & 1 \end{bmatrix}$$

AFR2 (1,3) should now contain the x coordinates of point E and AFR2(2,3) should now contain the γ coordinates of point E.

Let function $s(\gamma)=AFR2(1,3)(x\text{ coordinate})$ \quad (4)

Let Function $t(\gamma)=AFR2(2,3)(y \text{ coordinate})$ (5)

It follows that as both frame AFR2 and BFR4 are at the same point (E) that from equations 1 and 2 that $$s(\gamma)=f(\alpha,\beta) \quad (6)$$

$$t(\gamma)=g(\alpha,\beta) \quad (7)$$

Equations 6 and 7 represent 2 simultaneous equations with two variables. In order for the mechanism to exactly simulate the movement of the normal disc, it also follows the AFR2 and BFR4 must be equal.

$$AFR2=BFR4 \quad (8)$$

It can be shown that for this to occur that as well as equations 6 and 7 holding true. It also follows that.

$$\lambda=\alpha+\beta \quad (9)$$

Figure 6:
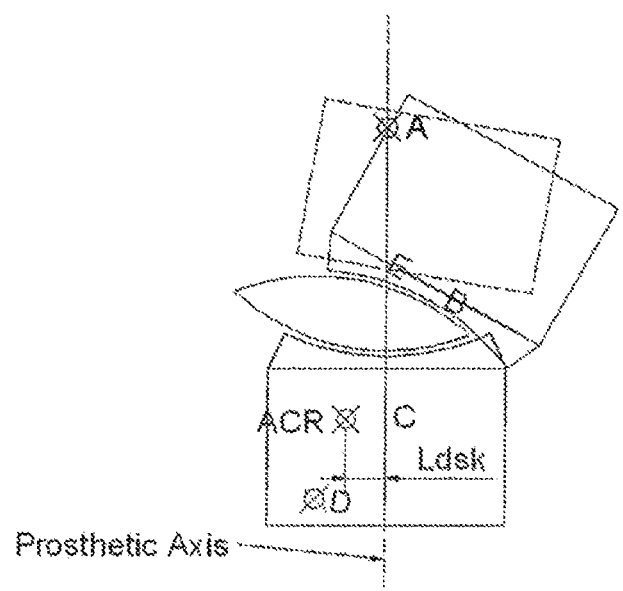
FIG. 6 shows a schematic of a bi-convex core prosthesis with an upper vertebrae in kyphosis.
Figure 7:
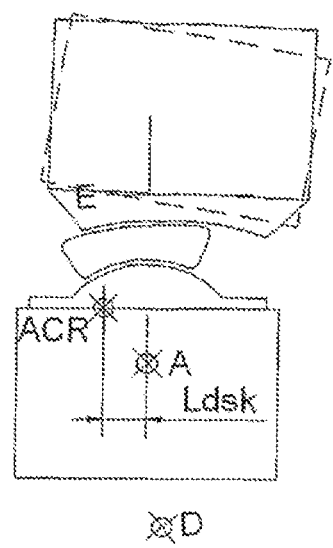
FIG. 7 shows a schematic of a convex/concave core prosthesis with the upper vertebrae in kyphosis.

It can be shown by numerical means that there are no real solutions that satisfy equations 6, 7 and 8. For a given angle γ that a normal disc will flex, the solutions for angles α and β are such that the prosthesis will be positioned in relative Kyphosis or Lordosis. FIG. 6 represents the effect of an attempt to flex an existing prosthesis with a biconvex core by 10 degrees with the constraint (constraint 1) being that point E is the same as the normal prosthesis. The solution to equations 6, 7 and 8 result in α equaling −10.72° and β equaling −18.26°. The dashed line represents a real disk rotating by 10° about ACR, this position represents the kyphotic solution to keep points E with the same co-ordinates. This position is the position of 0 ligament stretch (ZLS). FIG. 7 represents the effect of an attempt to flex a prosthesis with a core with a convex uppersurface and a concave lower surface by 10 degrees with the constraint (constraint 1) being that point E is the same as the normal prosthesis. The solution to equations 6, 7 and 8 result in a equaling 5.71° and β equaling −1.11°. The dashed line represents a real disk rotating by 10° about .ACR, this position represents the kyphotic solution to keep points E with the same co-ordinates, Though the position of kyphosis is significantly less than the biconvex core prosthesis. This position is the position of zero ligament stretch (ZLS).

In FIG. 7 the effect of attempting to extend a prosthesis by 10° is shown. Solutions to equations 6, 7 and 8 result in a equaling −1.55° and β equaling 4.75°. The dashed representation of the upper vertebrae again represents a real disk rotating by 10° about .ACR. This position represents the Lordotic solution to keep points E with the same co-ordinates. This position represents the 0 ligament stretch position (ZLS).

There are other ways of adding a constraint to the assembly. The other useful constraint is to constrain the lower end plate of the upper vertebrae to be parallel with the lower end plate of the upper vertebrae in the 'normal' situation and to minimize the distance between them. This can be achieved by rotating frames BFR4 and AFR2 by gamma degrees about the global reference frame AFR1 to produce two new frames AFR3 and BFR5

$$AFR3 = \begin{bmatrix} \cos\gamma & -\sin\gamma & 0 \\ \sin\gamma & \cos\gamma & 0 \\ 0 & 0 & 1 \end{bmatrix} \cdot AFR2$$

$$BFR5 = \begin{bmatrix} \cos\gamma & -\sin\gamma & 0 \\ \sin\gamma & \cos\gamma & 0 \\ 0 & 0 & 1 \end{bmatrix} \cdot BFR4$$

For both end plates to be parallel $$AFR3(1,1)=1(\cos(0)=1) \quad 10$$

and $$BFR5(1,3)=AFR3(1,3)=0 \quad (11)$$

as both x coordinates must be the same (zero)

Figure 8:
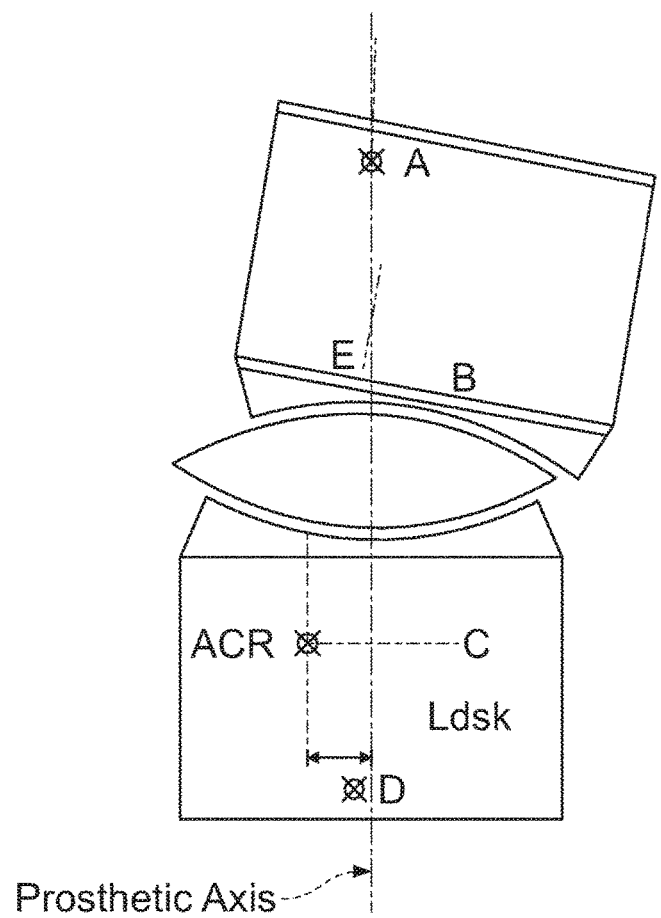
FIG. 8 shows a schematic diagram of a biconvex prosthesis with the upper vertebrae under the constraint of maximum ligament stretch (MLS)
Figure 9:
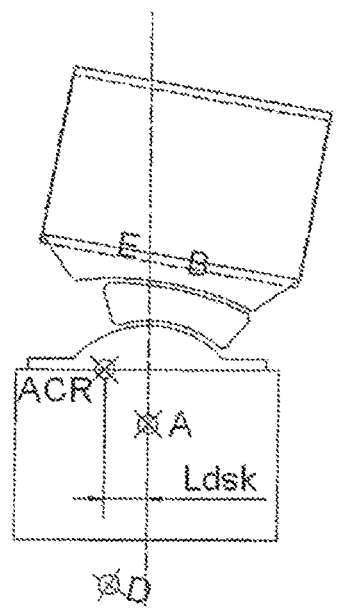
FIG. 9 shows a schematic diagram of a prosthesis with a core having a convex upper surface and concave lower surface, with the upper vertebrae under the constraint of maximum ligament stretch (MLS)

FIG. 8 shows the effect of adding this constraint (constraint 2) to an existing prosthesis with a biconvex core and attempting to match a 10 degree of flexion from a 'normal' motion segment. It can be seen that with this constraint that the two upper vertebrae cannot superimpose and that a ligament joining points ACR to E must be stretched beyond its normal length. With the constraint that the end plates are parallel, solutions to equation 6, 7 and 8 result in α equaling −1.61° and β equaling −8.39°. The dashed lines represent the real disk rotating by 10° about .ACR and the resultant position represents the solution to keep points with the end plates parallel and with minimum distance between them. This constraint is therefore termed Maximal Ligament Stretch (MLS). FIG. 9 shows the effect of adding this constraint (constraint 2) to a prostheis with a core with a convex upper surface and a concave lower surface and attempting to match a 10 degree of flexion from a 'normal' motion segment. It can be seen that with this constraint that the two upper vertebrae cannot superimpose and that a ligament joining points ACR to E must be stretched beyond its normal length. With the constraint that the end plates are parallel, solutions to equation 6, 7 and 8 result in a equaling −12.68° and β equaling −2.68°. The dashed lines represent the real disk rotating by 10° about .ACR and the resultant position represents the solution to keep points with the end plates parallel and with minimum distance between them. This constraint is therefore termed Maximal Ligament Stretch (MLS).

In FIGS. 6 and 7 the Ligament joining ACR to E has no stretch and instead the prosthesis rotates at point E to cause a degree of Kyphosis or Lordosis. This constraint is defined a Zero ligament stretch (ZLS)

In the cervical spine there is good anatomical evidence that there is only a weak posterior longitudinal ligament and the main lateral ligaments diverge from near the normal Anatomical centre of rotation (ACR) for that vertebrae. As the anterior longitudinal ligament has, by necessity, been destroyed by the surgical approach, The main ligamentous constraint in the cervical spine is approximated by Ligament ACR-E. In the absence of an effective posterior longitudinal ligament, there is reason to believe that a cervical disc prosthesis of the type shown in FIG. 6 would behave as if the constraint to movement was that of the ZLS variety, and there should be a tendency to kyphosis with flexion and lordosis/retrolisthesis in extension.

In the lumbar spine the posterior longitudinal ligament is much tougher. The lumbar spine therefore would preferentially attempt, to stretch the ligament ACR-E by using the constraint MLS. The annulus fibrosis would rarely allow this and the theory would suggest that flexion would be limited.

Whatever the particular case the real constraints in a given disc space will be a combination of the constraints ZLS and MLS. The difference in the angle achieved by the vertebrae and the desired angle (Gamma −(alpha+beta)) in the ZLS situation (Delta A) will be a measure of the prostheses inability to match the normal motion required. The difference between the length of ligament ACR-E and the desired length (Delta L) will also be a measure of the prostheses inability to match the normal motion required.

The mathematical equations developed above will enable design variables in a 2 articulation prosthesis to be optimized so as to minimize either Delta A or Delta L or both. By minimizing Delta A or Delta L the prosthesis will have a better chance of optimally simulating normal.

By the use of simulations using the above mathematical analysis the following holds.

Delta A is minimized to virtually nil by reducing variable Ldsk to zero. This has the effect of moving the prosthetic axis posteriori so that the ACR lies on the Prosthetic Axis. In this position Delta A remains very small for all positions of the ACR that lie at or below the disk space on the prosthetic axis.

Delta A is minimized when the radii of the upper and lower prosthetic articulations are approximately equal.

Delta A is minimized when the radii of the articulations are larger and Delta A gets larger with smaller radii.

It is preferred that Delta A is between 3 and 5°.

The translation of the Core is larger when the Prosthetic Radii are larger and the translation is smaller when the radii are smaller, The disclosed prosthesis therefore seeks to.

Move the prosthetic axis to the posterior one third of the disc.

Select optimal radii of the upper and lower joints.

In making these changes two problems are created.

In some embodiments the core of the prosthesis is no longer symmetrical and was it to rotate, it may impinge on the spinal canal.

Because of the posterior positioning of the prosthetic axis the core is at risk of spinal cord impingement.

Based upon the Mathematical Process described above the prosthesis consists, briefly, of two end plates, an intermediate mobile core and a separate anterior band for attachment to the upper and lower vertebrae.

FIGS. 13A to 13E show another embodiment of the invention in which the prosthesis consists of a core 50 having concave upper and lower surfaces 51, 52. An upper plate 53 has a convex lower surface 54 and lower plate 55 has an upper convex surface 56.

The lower surfaces 52, 56 are cylindrical from one side to the other (rotational and translational movement) rather than completely spherical, whereas the top surfaces 51 and 54 are completely spherical allowing for universal movement as opposed to backwards and forward movement as with the lower surfaces.

An additional feature of the prosthesis 49 shown in these FIGS. is the provision of upper and lower vertical ridges 57, 58 which are centrally located and adapted to fit into grooves created in the bottom surface of the upper vertebrae and the upper surface of the lower vertebrae. As shown more clearly in FIG. 11 the core 50 and upper plate 53 and lower plate 55 have the prosthetic axis 60 moved to the posterior H of the prosthesis so that the centre of the upper radius of curvature (CUPR) A and the centre of the lower radius of curvature (CLPR) D are aligned on the vertical axis through the ACR. As with the previous embodiment a major portion 61 is located forward of the axis 60 and a minor portion 62 is located behind it. Furthermore, the minor axis of the core 50 is aligned with the vertical axis 61. In addition the anterior and posterior vertical edges of the core 50 are flat and aligned in parallel with the minor axis 64.

The effect of attempting to flex the prosthesis 49 by 10° with the constraint being parallel end plates and full ligament stretch results in solutions to equations 6, 7 and 8 providing α with an angle of −6.87° and β with an angle of 3,13°.

Figure 11:
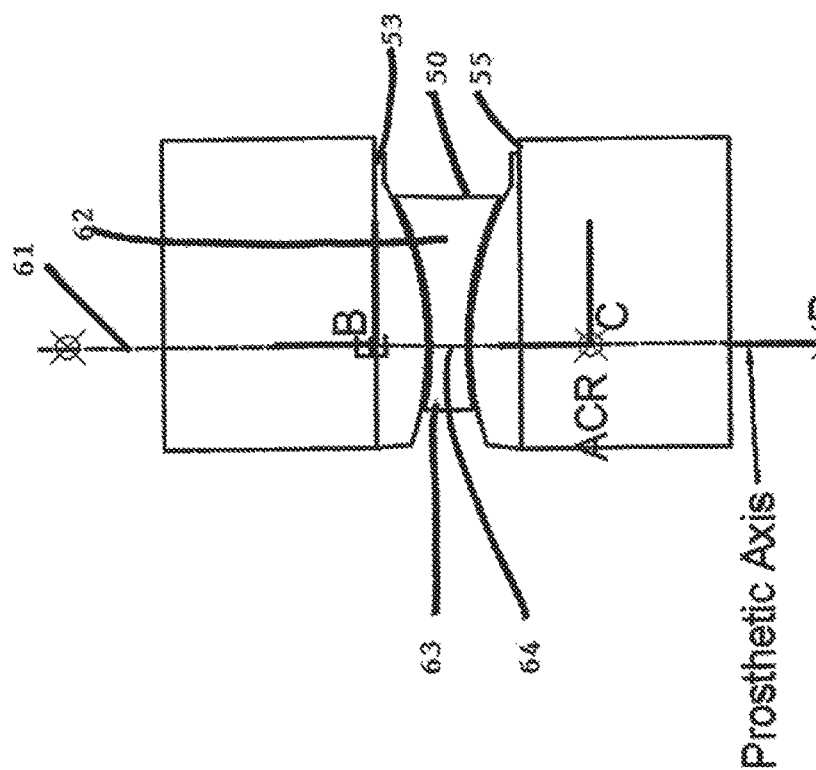
FIG. 11 shows a prosthesis according to another embodiment of the present invention with the upper vertebrae and lower vertebrae at rest.
Figure 12:
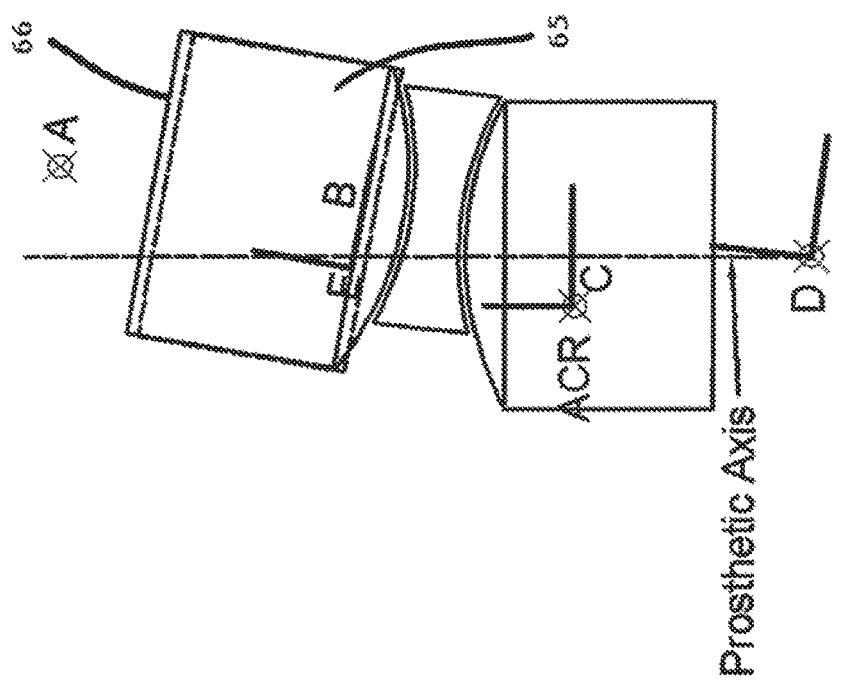
FIG. 12 shows the prosthesis shown in FIG. 11 with the upper vertebrae rotated by 10°.

In FIG. 12 an upper vertebrae 65 rotated through angles α and β are almost coincident with vertebrae 66 represented in dash line and corresponding to rotation by 10° (γ) about the ACR. This position represents the solution to keep points with the end plates parallel and with minimum distance between them. This corresponds to the position of maximum ligament stretch (MLS). The core of a bio-concave prosthesis as shown in FIGS. 11 and 12 move anteriorly in flexion. The amount of ligament stretch required to do this is less than when the prosthetic axis is at the mid point of the prosthesis and has therefore a design as shown in FIG. 10A and FIG. 10B. In this configuration the effect of attempting to flex a prosthesis by 10° with the constraint being parallel end plates and full ligament stretch results in solutions to equations 6, 7 and 8 providing α with an angle of −6.94° and β with an angle −3.06°. The prosthesis shown in this example represented by item 70 is symmetric about its minor axis which also in a state of rest coincides with the vertical axis of the upper and lower vertebrae 71, 72. FIG. 10B again shows the effect of moving upper vertebrae 71 through angles α and β compared to an upper vertebrae rotating by 10° relative to the ACR. It can be seen that movement possible by upper vertebrae 71 does not approximate movement of a real vertebrae 74 as well as prosthesis as designed with a prosthetic axis/minor axis coincident with the vertical axis through the ACR.

Figure 14:
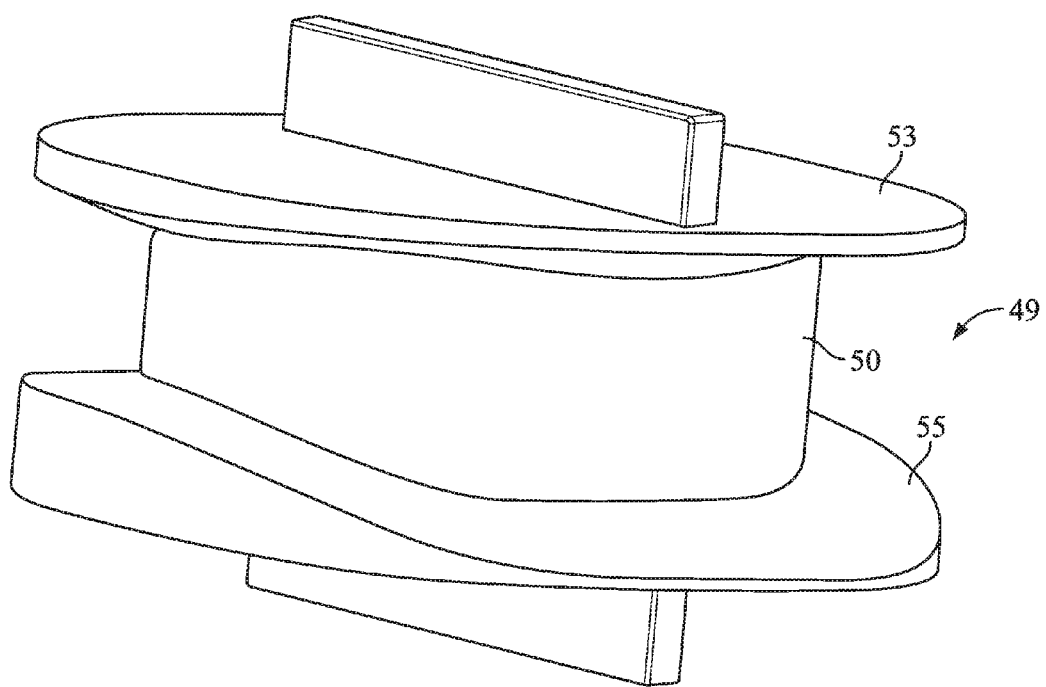
FIG. 14 shows an angled view of a prosthesis according to another embodiment of the present invention.

FIG. 14 shows an angled view of the prosthetic device 49 with core 50, upper plate 53 and lower plate 55.

Figure 15A:
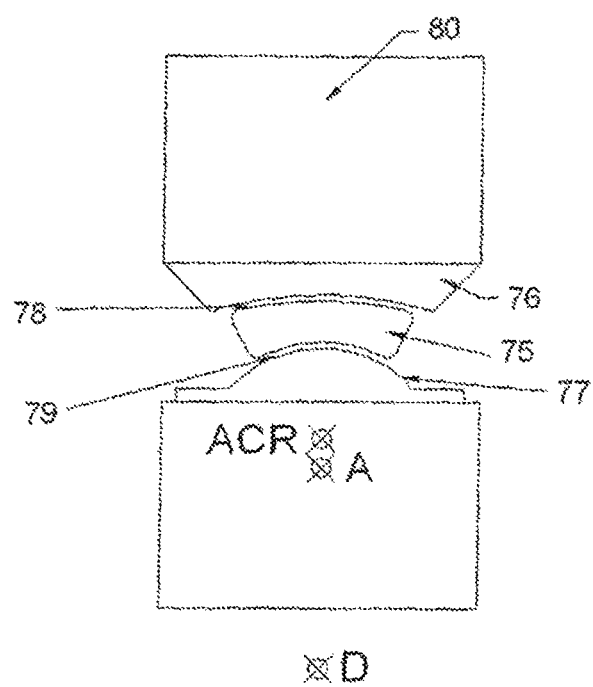
FIG. 15A shows a side schematic view of a prosthesis according to another embodiment of the invention with upper and lower vertebrae in a rest position.
Figure 15B:
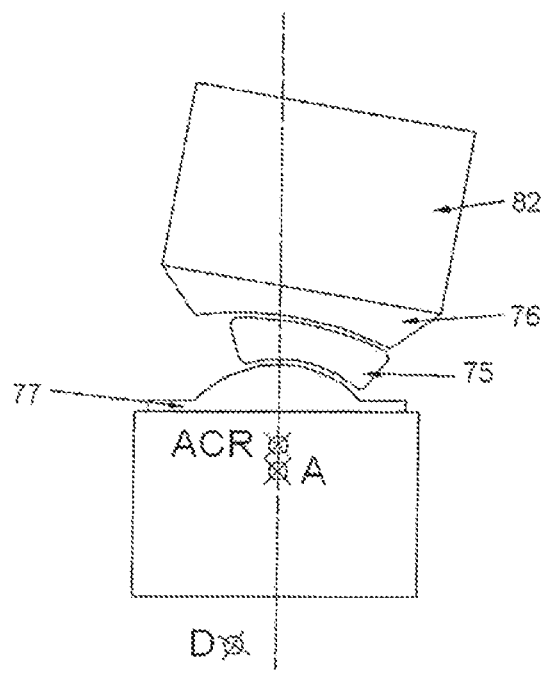
FIG. 15B shows the prosthesis in FIG. 15A with the upper vertebrae rotated 10°.

FIGS. 15A and 15B show an alternative embodiment of the invention in which a prosthesis is provided with a core 75 with upper plate 76 and lower plate 77. The core 75 has an upper convex surface 78 and a lower concave surface 79. As with the embodiments described in relation to FIGS. 12 and 13, the minor axis 80, the prosthetic axis coincides with the vertical axis through the ACR of the lower vertebrae 81. Because the lower surface 79 is convex it is significantly smaller than the upper convex surface 78. Likewise the lower surface of the upper plate 76 is concave and has a matching configuration to surface 78. The lower plate 77 has a convex upper surface which is longer than the matching concave surface 79 to allow movement by the core 75 there over backwards or forwards.

FIG. 15B shows how rotation of the upper vertebrae 82 results in relative movement between upper plate 76 and core 75 as well as relative movement between core 75 and lower plate 77.

As with the embodiments shown in FIG. 13 the prosthetic axis is asymmetric and a major portion of the core 75 is located forward of the prosthetic axis.

Figure 16:
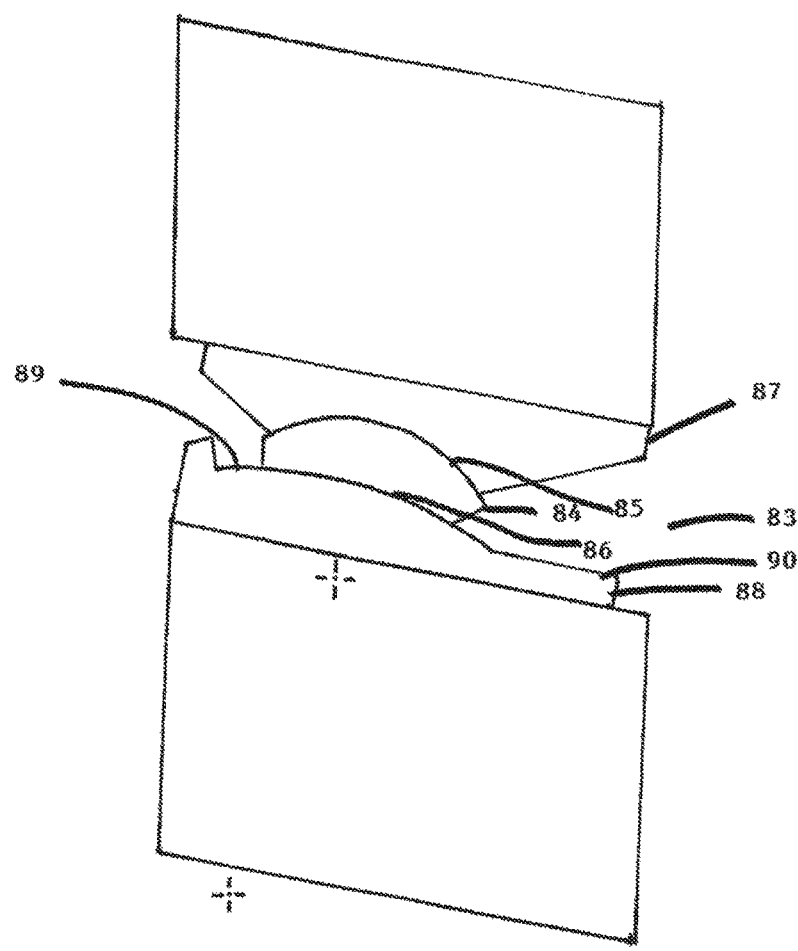
FIG. 16 shows a schematic side view of a prosthesis according to another embodiment of the present invention.

FIG. 16 shows a side view of another prosthesis 83 consisting of a core 84 having an upper convex surface 85 which has a lower radius of curvature compared to a lower concave surface 86. In this embodiment both the upper and lower surfaces 85, 86 have centres of radius of curvature which are located below the core 84.

Upper plate 87 has a lower concave surface matching that of surface 85 and lower plate 88 has an upper convex surface 89 which is much longer than the length of the surface 86 to allow reasonable travel backwards and forwards. In addition the convex surface 89 of the lower plate 88 extends into a straight horizontal flat surface 90. This effectively prevents forward travel of the core 84 beyond the end of the convex surface 89.

Figure 17:
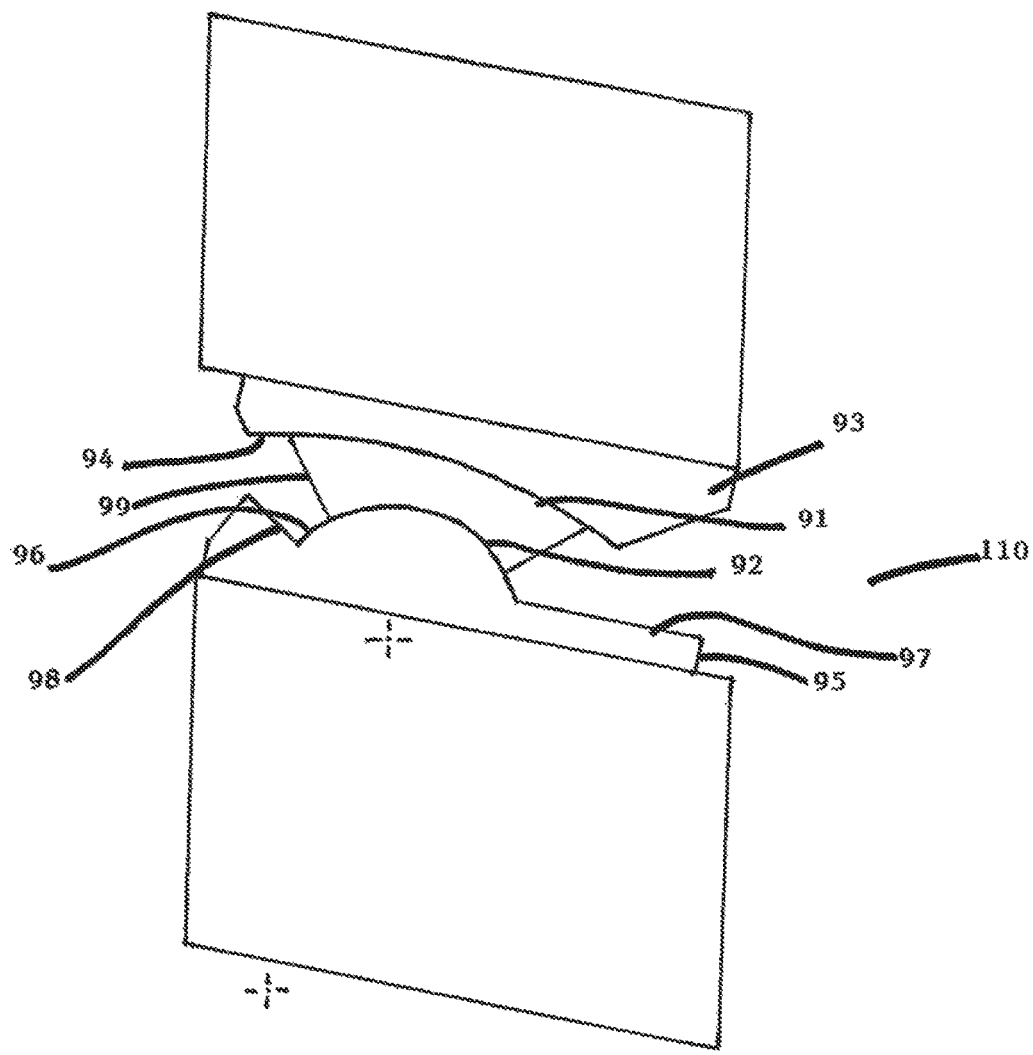
FIG. 17 shows a schematic side view of a prosthesis according to a further embodiment of the present invention.

FIG. 17 shows a prosthesis 91 which is similar to prosthesis 83 except that the upper surface 92 has a greater radius of curvature than the lower surface 93. In addition therefore the lower surface of the upper plate 93 is concave and longer in length than its co acting upper surface 91. Lower plate 95 has a convex surface which is longer in length than the co-acting concave surface 92. In addition at a rearward end of the convex surface 96, an upwardly angled straight section 98 is provided as a method of stopping movement of the core 99 beyond the end of the convex surface 96.

The forward end of convex surface 96 also extends into a horizontal straight section 97 which serves to prevent the core 99 moving beyond the front end of the curved surface 96.

It should be noted that the prostheses 83, 91 are more realistically represented in FIGS. 16 and 17 as being interposed between upper and lower vertebrae which have a more trapezoidal shape rather than a rectangular shape. Thus although surfaces 90 and 97 and previously described surfaces have been described as being horizontal, in fact they are slanted and instead are generally parallel to the general orientation of the upper and lower faces of the upper and lower vertebrae. It should also be noted that surfaces 90 and 97 can be angled upwardly or even downwardly as long as they prevent forward movement of the core 84, 99.

Figure 18:
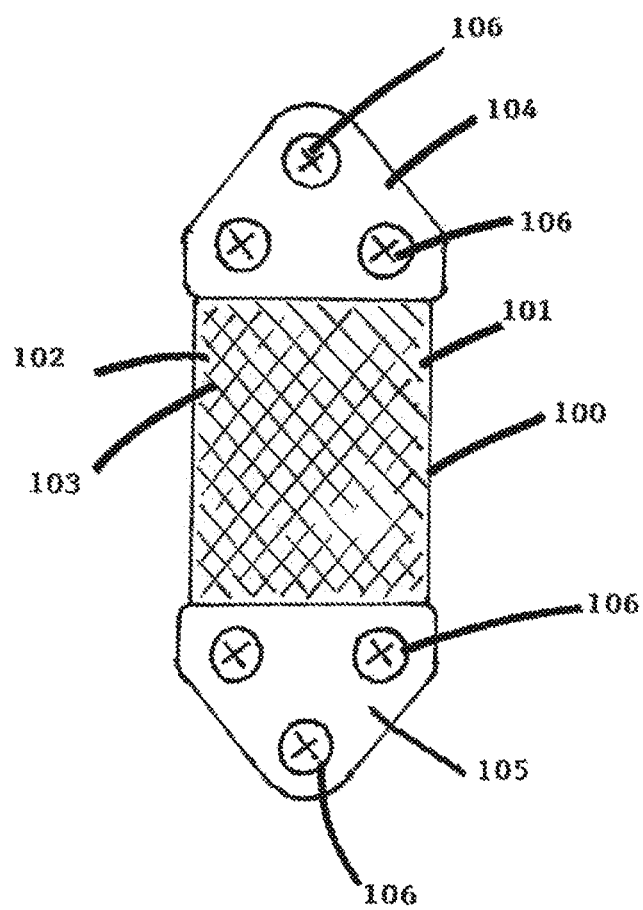
FIG. 18 shows a front view of a ligament band of the present invention according to one embodiment.

The different prosthesis which have been thus far described have concentrated on characteristics which emulate an invertebral disk. An additional component useful for a prosthesis designed to emulate characteristics of an invertebral disk include a band 100 shown in FIG. 18 which is designed to closely simulate actions of ligature and in one embodiment also provides a stop for forward movement of a prosthetic core.

The band 100 consists of a woven fabric 101 consisting of filaments of wafts and wefts creating a weave with a grid like pattern. Upper and lower ends 102, 103 are provided with connecting plates 104, 105 each with holes 106 for screws to be inserted through for attachment to upper and lower vertebrae respectively.

The woven fabric 101 is preferably designed to encourage cellular growth in the interstitial spaces between the threads/filaments and to ultimately result in ligatures growing between the upper and lower vertebrae.

According to one embodiment the band is in the form of a prosthetic ligament made from a woven and absorbable material of appropriate stiffness. The woven material is designed to allow ingrowth of fibrous tissue to replace the function of the prosthetic ligament as it is reabsorbed.

According to one embodiment the band is in the form of a gauze made of wire or polymeric material.

It is preferred that the band is able to elongate or contract in a similar fashion to a ligament.

With regard to materials used for the different prosthesis described above, the end plates may be made from a metal such as titanium, cobalt-chromium steel or a ceramic composite. Typically they have a roughened planar surface which abuts against the adjacent surface of the vertebrae. To assist with fixing the plates to the vertebrae, they may be provided with a fin or ridge as described in the embodiment shown in FIGS. 13 and 14 or they may be provided with curved surfaces for bearing on an adjacent vertebral body end plate.

The upper and lower surfaces of the core as well as the adjacent curved surfaces of the upper and lower end plates are preferably smooth to enhance articulation. The central core may be made from similar materials to those used for the end plates, but may also be made from a plastic such as UHMW polyethylene or polyurethane composite.

It is preferred that the radius of curvature of each of the curved surfaces of the prosthesis is in the range of 5 to 35 mm.

The foot print of the prosthesis end plates may be of a variety of shapes but will be optimised to minimise the risk of subsidence into the adjacent vertebral bone.

Although the various articulation surfaces of the core and upper and lower plates have been described in relation to concave and convex surfaces, it should be noted that other surface profiles are also included in the invention.

For example the co acting surfaces of the core and the lower plate could be ellipsoid instead of cylindrical to provide restricted relative movement therebetween.

Previously a mathematical explanation has been provided of the behaviour of an artificial disk prosthesis having dual articulation. Different embodiments of the prosthesis have been described covering each of the permutations of possible upper and lower surface profiles. These have included biconvex, biconcave as well as convex upper and concave lower and concave upper and convex lower. The equations previously outlined described the position and orientation of a moving upper vertebrae on a fixed lower vertebrae with the dual articulating prosthesis located therebetween. Movement of the upper vertebrae relative to the upper surface of the prosthesis and movement of the lower surface of the prosthesis relative to the lower vertebrae have been described with reference to constants and by variable angle of rotation of variables $\alpha$ and $\beta$. The orientation of the upper vertebrae is described by:

$$\cos^{-1}(\cos \alpha \cdot \cos \beta - \sin \alpha \cdot \sin \beta)$$

The position of a point E immediately above the centre of rotation of the disc space and on the lower edge of the upper vertebrae is given by the following equations:

$$x(\alpha,\beta) = -(\sin \alpha \cdot \cos \beta + \cos \alpha \cdot \sin \beta) \cdot Ldsk + (\cos \alpha \cdot \cos \beta - \sin \alpha \cdot \sin \beta) \cdot Cdsk - \cos \alpha \cdot Bdsk + Pdsk$$

$$y(\alpha,\beta) = -(\sin \alpha \cdot \cos \beta + \cos \alpha \cdot \sin \beta) \cdot Ldsk + (\cos \alpha \cdot \cos \beta - \sin \alpha \cdot \sin \beta) \cdot Cdsk - \cos \alpha \cdot Bdsk + Pdsk)$$

Where Constants define the size and functional type of the prosthesis.

Depending on the relative sizes of parameters Ldsk, Cdsk, Bdsk and Pdsk there are 4 distinct types of prosthesis that are described:

These are: (described by the core shape)
1. Biconvex
2. Biconcave
3. Convex top concave bottom with the top radius greater than bottom radius
4. Convex top concave bottom with the bottom radius greater than the top radius Equations 1-3 describe the kinematics of these 4 prosthesis.

The length of a line joining the COR to point E is $$l(\alpha,\beta) = \sqrt{x(\alpha,\beta)^2 + y(\alpha,\beta)^2}$$

Wherein $\alpha$ is the angular displacement of the upper part relative to the middle part, $\beta$ is the angular displacement of the middle part relative to the lower part and l is the ligature joining a part of the upper part with the centre of rotation of the skeletal structure (or prosthesis) when in use and where $x(\alpha, \beta)$ and $y(\alpha,\beta)$ are different functions.

Preferably "ligature" includes any elongate member particularly one with a degree of extension of stretch and contraction or compression.

The values of alpha and beta can be calculated that produce a minimum value for l. l can be considered to be the lateral ligament of the spinal motion segment. As this is elastic it can be seen that it will behave as a spring and consequently will have the lowest elastic potential energy when l is smallest. An equilibrium position can be calculated when l is either a minimum or a maximum. Mathematically this can be defined as the gradient vector being zero:

$$\nabla l(\alpha, b) = \begin{bmatrix} \frac{\delta \ell}{\delta \alpha} \\ \frac{\delta \ell}{\delta \beta} \end{bmatrix} = \begin{bmatrix} 0 \\ 0 \end{bmatrix}$$

Under the circumstances of a zero gradient vector the prosthesis will have a zero change in elastic potential energy for infinitesimal changes in α and β and the prosthesis will be in an equilibrium position. However when this equilibrium position is a maximum value for l it can be seen that small perturbations in α or β will tend to cause l to decrease and the equilibrium position is unstable. Mathematically this can be described as:

$$\begin{bmatrix} \frac{\delta^2 \ell}{\delta \alpha} \\ \frac{\delta^2 \ell}{\delta \beta} \end{bmatrix} = \begin{bmatrix} -ve \\ -ve \end{bmatrix}$$

or $$\begin{bmatrix} \frac{\delta^2 \ell}{\delta \alpha} \\ \frac{\delta^2 \ell}{\delta \beta} \end{bmatrix} = \begin{bmatrix} +ve \\ -ve \end{bmatrix}$$

or $$\begin{bmatrix} \frac{\delta^2 \ell}{\delta \alpha} \\ \frac{\delta^2 \ell}{\delta \beta} \end{bmatrix} = \begin{bmatrix} -ve \\ +ve \end{bmatrix}$$

Under these circumstances it would be possible for the prosthesis to be precisely balanced and be in equilibrium, though small perturbations would cause it to rapidly adopt a position of maximum flexion or extension.

It can be shown that prostheses 1) and 4) have unstable equilibrium positions. This situation occurs when matching an on axis or off axis COR. By increasing the radii of the upper and lower articulations the value of the gradient vector will be less negative and the tendency to adopt a position of maximum flexion or extension will be diminished.

Prostheses 2) and 3) however, have the property of having a positive second partial derivative of l.

$$\begin{bmatrix} \frac{\delta^2 \ell}{\delta \alpha} \\ \frac{\delta^2 \ell}{\delta \beta} \end{bmatrix} = \begin{bmatrix} +ve \\ +ve \end{bmatrix}$$

At the equilibrium position defined by $$\nabla l(\alpha, \beta) = \begin{bmatrix} \frac{\delta \ell}{\delta \alpha} \\ \frac{\delta \ell}{\delta \beta} \end{bmatrix} = \begin{bmatrix} 0 \\ 0 \end{bmatrix}$$

In other words there exist values of α and β that cause an equilibrium when l is a minimum. This equilibrium is stable and self correcting- or self centering because any tendency to perturb the prosthesis from the equilibrium position will have a tendency to cause l to lengthen and therefore increase the elastic potential energy of the system.

Prostheses 2) and 3) therefore have stable equilibrium positions and are self correcting or self centering.

When attempting to match a COR that is on axis with the prosthesis the equilibrium position is in the neutral position (when α=β=0). When matching an off axis COR the equilibrium position will now be located away from the neutral position (when α≠ββ0)—when matching a CR that is anterior to the prosthesis axis the equilibrium position will be in extension and when matching a CR that is posterior to the prosthetic axis the equilibrium position will be in flexion.

When the values of the radii of the upper and lower articulations are large the equilibrium position changes due to matching an offset will be lessened.

Figure 20A:
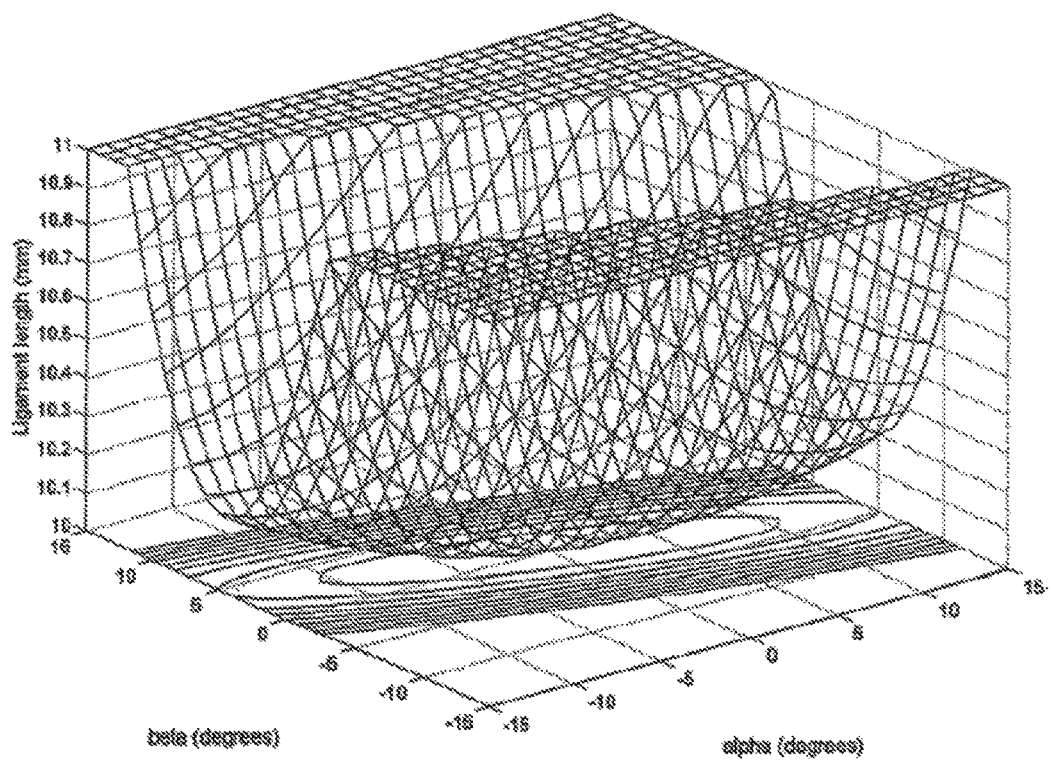
FIGS. 20A and 20B show a three dimensional graphical analysis of different positions of a prosthesis having a core with a convex upper surface and convex lower surface in accordance with an embodiment of the present invention.

FIG. 20A shows a graphical plot in three dimensions of the ligament length l versus β and a for a prosthesis core with a convex upper surface and a concave lower surface where the radius of curvature of the upper surface of greater than that of the lower surface. As an example the upper radius is 36 mm compared to 12 mm for the lower radius.

It can be seen from FIG. 20A that the three dimensional graph shown indicates a minimum ligament length as represented by a trough in the graph.

Figure 19A:
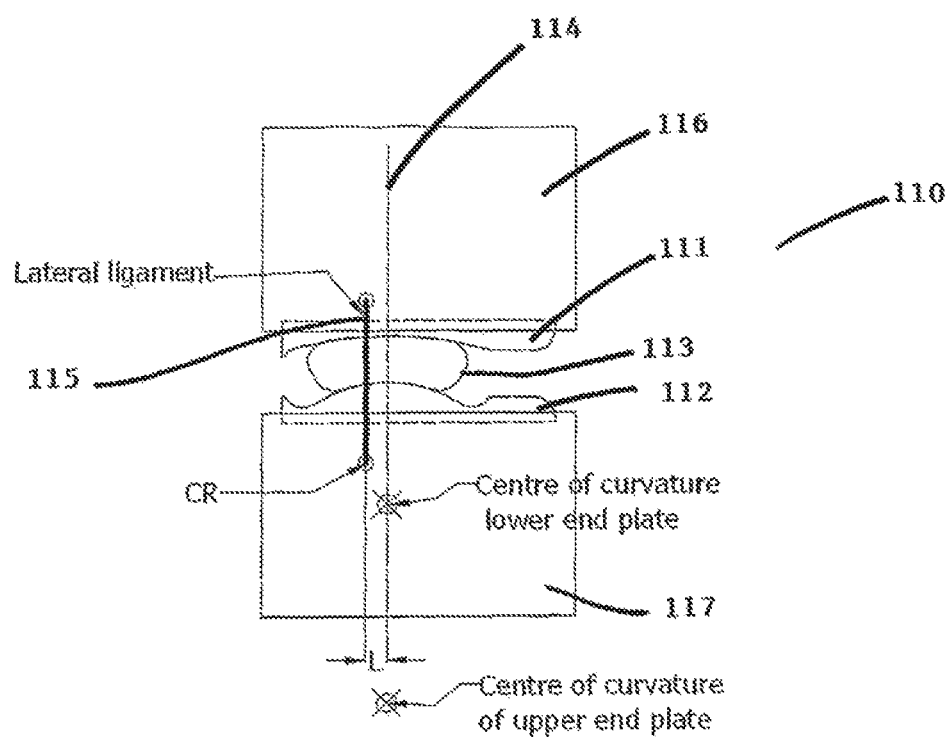
FIG. 19A shows a schematic cross-sectional end view of a prosthesis in an equilibrium position according to another embodiment of the invention.
Figure 19B:
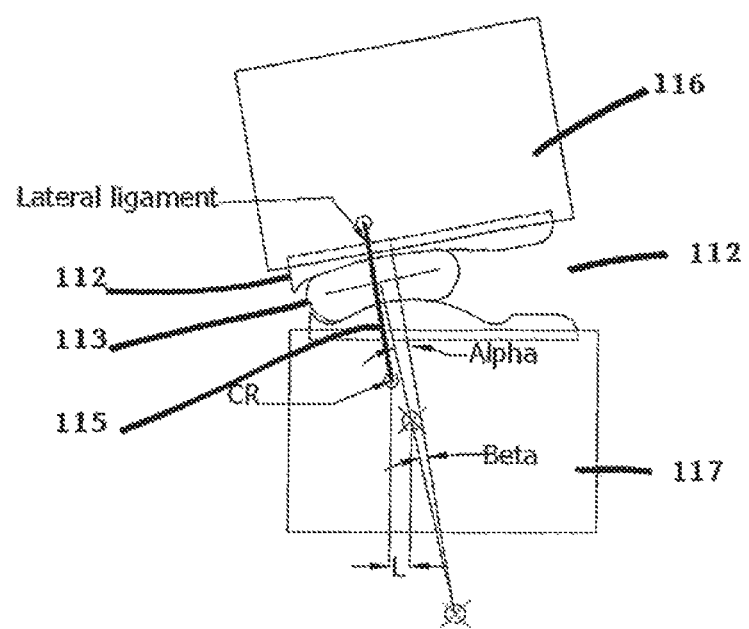
FIG. 19B shows the prosthesis of FIG. 19A in an unstable position.

In this Figure there is zero, X and Y offset, which means the prosthesis axis is aligned with the patient's centre of rotation and corresponds to L in FIGS. 19A and 19B.

Figure 20B:
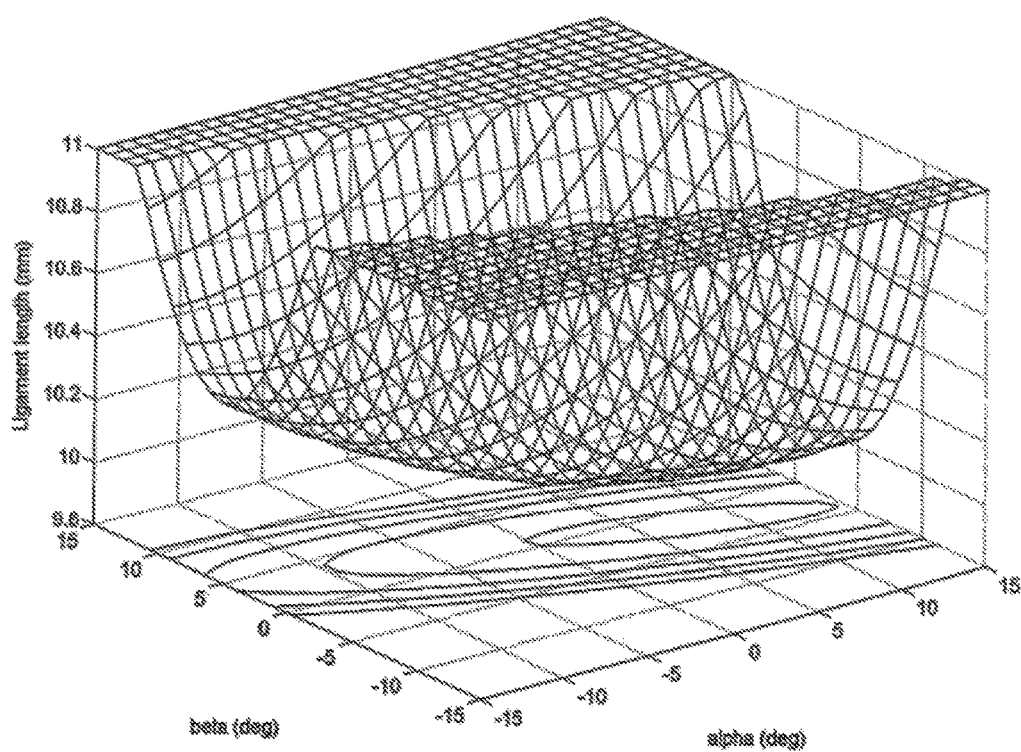

FIG. 20B shows the effect of introducing a value for L of 1 mm for the same type of prosthesis shown in FIG. 20A. The equilibrium position moves in the opposite direction to L. The mathematical method can be used to optimise this change in equilibrium position and make the prosthesis less sensitive to changes in Y offset (L) or X offset (moving the patient's CR inferiorly).

Figure 21:
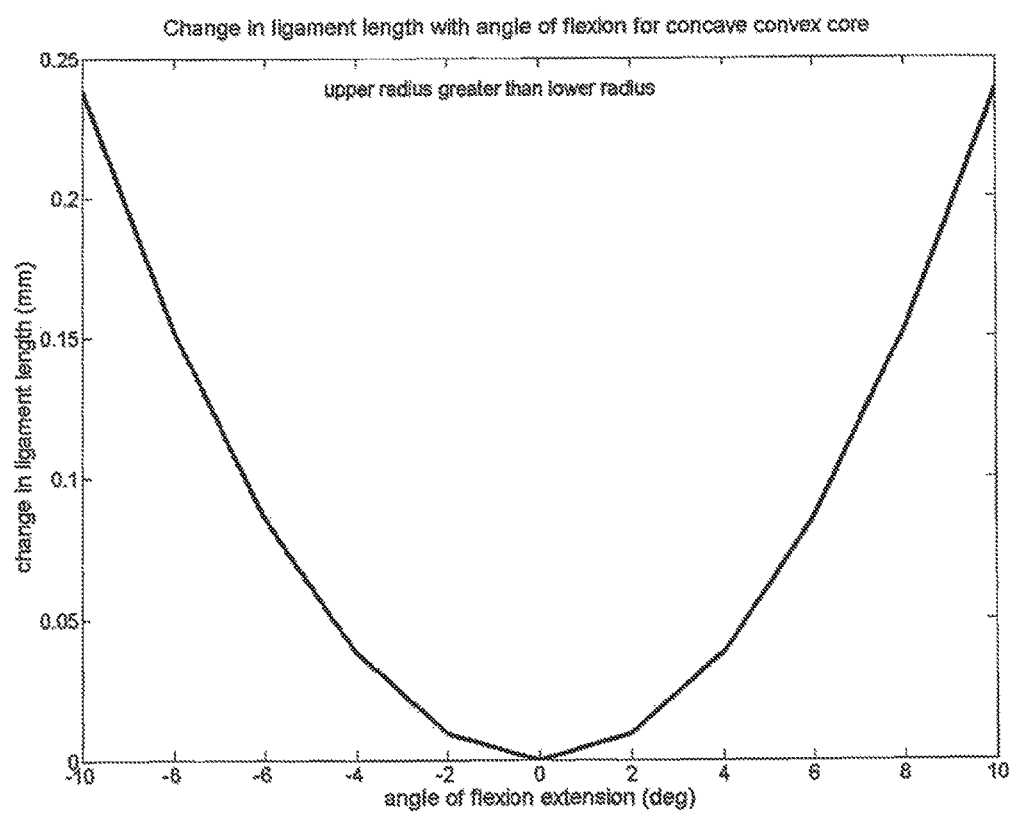
FIG. 21 shows a 2D graphical representation of the prosthesis analysed in FIG. 20.

FIG. 21 shows a two dimensional view of the change in ligament length with angle of flexion for the prosthesis referred to in FIG. 20A. In this FIG. it can be seen that there is a clear trough around the centre of rotation represented by angle of flexion extension 0. This graph clearly shows that any movement of the prosthesis away from the centre of rotation results in extension of the ligament length and therefore a natural tendency for the ligament to want to return to its minimum length at the centre of rotation.

Figure 22:
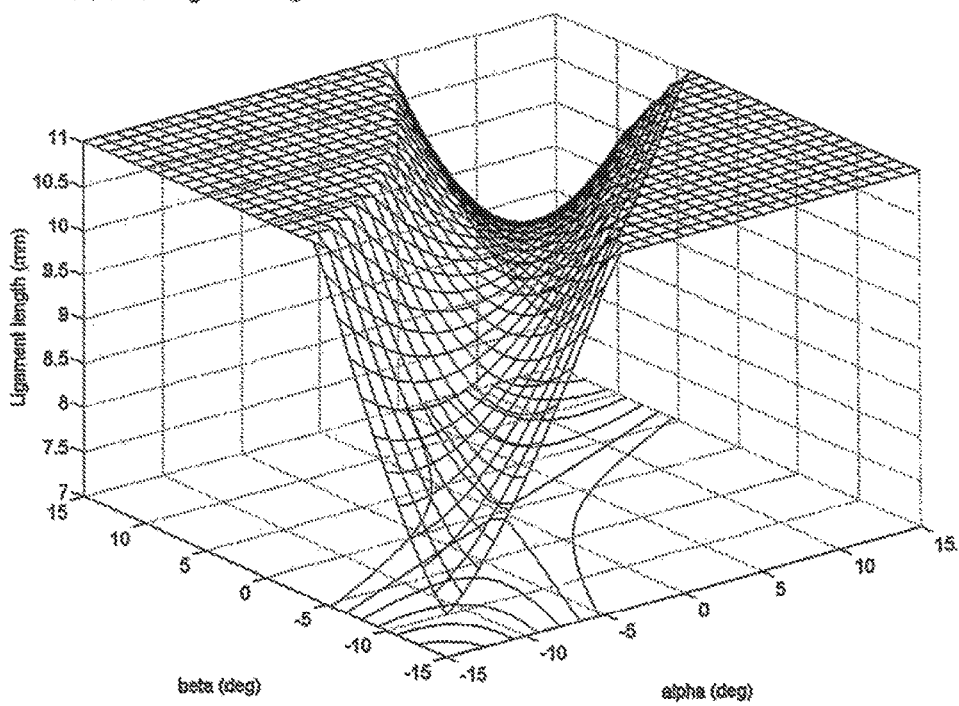
FIG. 22 shows a 3D graphical analysis of a bi-convex prosthesis.
Figure 23:
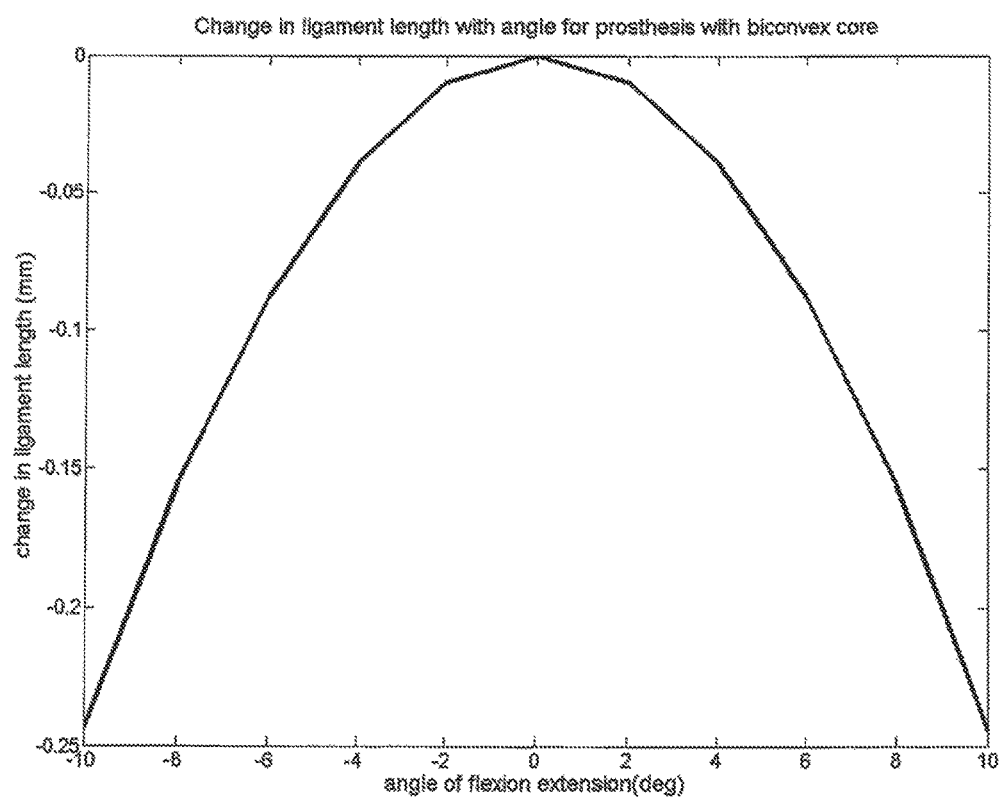
FIG. 23 shows a 2D graph of ligament length vs angular movement for a dual convex prosthesis.

The above contrasts with a prosthesis with a biconvex core. A graphical solution to the mathematical equation outlined above is shown in FIG. 22 for a biconvex core. It should be apparent from this graphical analysis that there is no minimum ligament length which provides a point of equilibrium. In fact the two dimensional graphical representation shown in FIG. 23 shows how the point of equilibrium is located about the centre of rotation of the biconvex core and shows that any movement of the core away from the centre of rotation results in a decrease in the ligaments length and therefore a tendency for the core to move away from the point of equilibrium.

Figure 24:
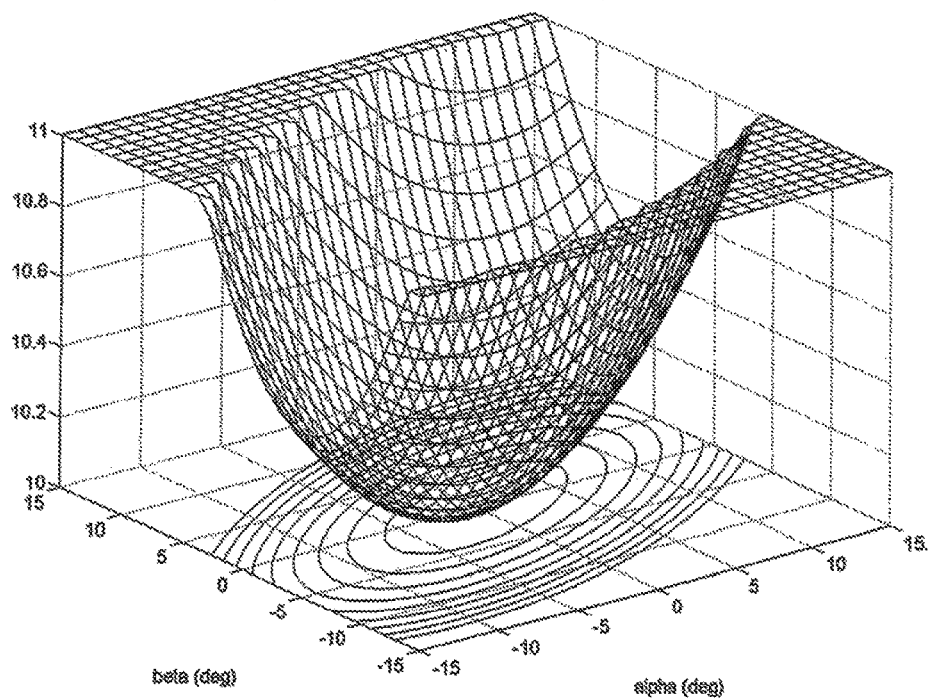
FIG. 24 shows a 3D graphical analysis of a Bi-concave prosthesis according to a different embodiment of the present invention.

FIG. 24 shows another embodiment of the invention in which the prosthesis has a biconcave core. As with the embodiment shown in FIGS. 20A, 20B and 21 in this embodiment there is a point of equilibrium about the centre of rotation for the core. This point of equilibrium corresponds to the minimum ligature length and hence provides a natural tendency for the core to return to the point of equilibrium if there is movement away from the centre of rotation.

In another embodiment the variation in ligament length for a biconcave prosthesis with the upper radius equal to 36 mm and the lower radius equal to 36 mm with Y offset and X offset being zero. It can thus be seen that with equal radius the graphical representation of the mathematical model shows there is no tendency for movement of the prosthesis away from the equilibrium position to result in a movement back to the equilibrium position.

The two dimensional graphical representation which is not shown has a similar appearance to FIG. 21.

From the above it should be clear that if it is desired to produce a prosthesis with a self correcting ability which results in a tendency of any movement away from a point of equilibrium to result in a natural urging of the prosthesis back towards the point of equilibrium, then the embodiment of the invention described in relation to FIGS. 20A, 20B, 21 and 24 provide suitable solutions. It is also noted however that the other embodiments of the invention which have been described may still be used even though they may not have this self-centering ability. This is because other alterations may be made to the overall prosthesis in order to keep movement of the prosthesis within predetermined boundaries.

All prostheses are able to match a COR that is on axis. When the COR is off axis they can only match by either stretching or shortening the lateral ligament (Delta L) or by adopting abnormal orientation (Delta A). Delta A and Delta L, for a given offset can be reduced by making the Radii Larger.

All prostheses are capable of pure translation. Prosthesis 2) does so with loss of disc height, Prosthesis 3) does so with a gain in disc height.

The Ideal prosthesis has
1 Stable equilibrium position
2 The best capacity to handle off axis CR
This is 2) or 3)

The preferred embodiment is 3) with as large radii as possible. This has the added advantage of resistance to pure translation (because the soft tissues would need to lengthen)

The second preferred embodiment is 2) this has the advantage of relatively unrestricted translation.

There may be clinical situations where either 2) or 3) are preferable.

The ratio of radii for prosthesis 3 can be set so that under a COR match to a physiologically normal centre of rotation there is equal arc travel between the top and bottom articulation. This can be achieved by $R1*alpha=R2*beta$ Where alpha and beta can be calculated for the CR match.

This will match wear for upper and lower articulations and is the most efficient use of the surface area of contact.

A capacity to calculate alpha and beta allows the prosthesis to be drafted.

An ideal range for of ratio for prostheses in the lumbar spine and cervical spines to achieve this is 3:1-10:1.

In the lumbar and cervical spines the preferred radii are 5 mm and 50 mm.

Prosthesis 2 does not allow the travel on each articulating surface to be equal. Preferably the mathematical model will be used for this prosthesis to allow an optimum choice of ratio of radii based on any desirable parameter such as the desired ratio of angles α and β. In the lumbar and cervical spines the ideal ratio is 2:1-1:2. In the Lumbar spine the preferred radii are between 8-40 mm for each radii. In the cervical spine the preferred radii are between 6-30 mm FIGS. 10A to 11B and 13A to 13F show a prosthesis having a biconcave profile. FIGS. 15A, 15D, 16 and 17 show a prosthesis with an upper convex surface and a lower concave surface. It is preferred that the version of the prosthesis shown in FIG. 17 is utilised as the radius of curvature of the upper surface is larger than that of the lower concave surface. It is also preferred that the lower surface of the upper plate has a matching profile to the upper surface of the prosthesis and the upper surface of the lower plate has a matching profile to the lower surface of the prosthesis. It should be understood however that this does not mean that the entire lower surface of the upper plate and upper surface of the lower plate have the matching profiles. Thus a reference to FIG. 19A shows one preferred configuration of a prosthesis having the preferred upper and lower surface profiles identified above. The prosthesis 110 shown is symmetrical about a central vertical axis and has smooth curved outer upper and lower edges. The prosthesis is shown offset rearwardly and hence with its core 113 retained within a rearward region of the upper and lower plates 111, 112.

The upper surface of the lower plate 112 has a rearward portion having a convex shape of matching configuration to the opposing concave profile of the core 113.

The apex of the convex region is offset rearwardly with respect to the centre of prosthesis. The convex region is symmetrical about its offset central vertical axis and on either side extends into a concave trough with the result that the overall profile of this region has the appearance of part of a sinusoidal curve.

Each of the troughs extend into upwardly curved surfaces on either side of the convex region and provide rearward and forward detents to limit forward and backward movement of the prosthesis relative to the lower plate.

The upper plate 111 has a rearwardly offset concave lower surface with a rearmost downwardly extending edge which is configured to limit rearward movement of the core 113 relative to the upper plate 111.

As can be seen from FIG. 19A the radius of curvature of the lower surface of the upper plate is larger than the radius of curvature of the upper surface of the lower plate. In each case the radius of curvature has a common origin which is located on the central vertical axis of the prosthesis at a virtual point below the prosthesis.

FIG. 19A also shows the core 113 in a stable equilibrium position aligned with the central vertical axis 114 which is rearwardly offset to the anatomical central axis.

A lateral ligament 115 is shown connected between upper and lower vertebrae 116, 117. The ligament 115 is offset by a distance L from the axis 114.

FIG. 19B shows how the prosthesis 112 is effected by backward rotational movement of the upper vertebrae 116 with respect to the lower vertebral disk 117.

As shown the lateral ligament 115 rotates about the centre of rotation (CR) and the upper plate 111 and core 113 rotate to an unstable position. Because of the difference in radius of curvature of the upper surface of core 113 and the lower surface the ligament 115 is stretched and there is a natural tendency for it to return to the equilibrium position shown in FIG. 19A. The difference in radius of curvature also means that the upper vertebral disk 116 will rotate and translate with respect to the lower vertebral disk 117.

By increasing the radius of curvature of the lower surface of the upper plate and hence the upper surface of the prosthesis it is possible to increase the stability of the prosthesis when in use if the COR of the prosthesis is offset from the ACR.

Desirably increasing the radius of curvature of the upper surface of the prosthesis and hence the lower surface of the upper plate enhances the ease with which the prosthesis is able to return to its equilibrium point centered about its central vertical axis.

According to one embodiment the further the central vertical axis of the prothesis is offset from the centre of rotation of the skeletal structure, the larger the radius of curvature of the upper surface of the prosthesis.

It is preferred that the radius of curvature of the upper surface of the prosthesis is between 30 and 50 mm in the lumbar spine and 20 and 40 mm in the cervical spine. As it is preferred that the ratio of the radius of curvature of the upper surface of the prosthesis compared to the lower surface of the prosthesis is within a predetermined range an increase in the radius of curvature of the upper surface of the prosthesis will result in a corresponding increase in radius of curvature of the lower surface of the prosthesis.

It is preferred that the length of the convex region of the upper surface of the lower plate (when measured from front to rear) is determined in accordance with typical travel allowed for a vertebral disk in a typical vertebral column.

It is preferred that all embodiments of the prostheses have a prosthetic axis that is set in the posterior ½ of the disc to as closely as possible match the normal physiological centre of rotation.

It is to be understood that, if any prior art publication is referred to herein, such reference does not constitute an admission that the publication forms a part of the common general knowledge in the art, in Australia or in any other country.

The invention claimed is:

1. A method of producing a prosthesis for vertebrae comprising providing a mathematical model for designing a prosthesis used to simulate kinematics of an intervertebral disk, using the mathematical model to produce a prosthesis comprising an upper part, a lower part, and a middle part, which prosthesis simulates kinematics of an intervertebral disk and wherein the upper part when the prosthesis is attached to upper and lower vertebrae simulates rotational and translational movements possible with an intervertebral disk.

2. The method as claimed in claim 1 wherein the simulation provided by the prosthesis includes tilting of the upper part relative to the anatomical centre of rotation of the lower vertebral disk and translational movement forward and back to an extent permissible for an upper vertebrae with an intervertebral disk.

3. The method as claimed in claim 2 wherein the prosthesis has an equilibrium position offset with respect to a central vertical axis through one of the prosthesis or anatomical central axis.

4. The method as claimed in claim 1 wherein the prosthesis upper part has a lower surface portion with a first radius of curvature, the middle part has an upper surface portion with a second radius of curvature and a lower surface portion with a third radius of curvature and the lower part has an upper surface portion with a fourth radius of curvature, wherein the centre of the radius of curvature for at least two surfaces is offset rearwardly with respect to a central vertical axis through the upper and lower parts.

5. The method as claimed in claim 1 wherein the middle part has an upper convex surface and a lower concave surface or an upper concave surface and a lower concave surface.

6. A method of producing a prosthesis for vertebrae comprising:
providing a mathematical model for designing a prosthesis used to simulate kinematics of an intervertebral disk;
using the mathematical model to produce a prosthesis comprising an upper part, a lower part, and a middle part, which prosthesis simulates kinematics of an intervertebral disk and wherein movement of the upper part with respect to the lower part when the prosthesis is attached to upper and lower vertebrae simulates rotational and translational movements possible with an intervertebral disk.

7. The method of claim 6, wherein the upper part has a lower surface portion with a first radius of curvature, the middle part has an upper surface portion with a second radius of curvature and a lower surface portion with a third radius of curvature, and the lower part has an upper surface portion with a fourth radius of curvature, and wherein the center of the radius of curvature for at least two surfaces is offset rearwardly with respect to a central vertical axis through the upper and lower parts.

8. The method of claim 6, wherein the prosthesis upper part has a lower surface portion with a first radius of curvature, the middle part has an upper surface portion with a second radius of curvature and a lower surface portion with a third radius of curvature, and the lower part has an upper surface portion with a fourth radius of curvature, and wherein the first radius of curvature is larger than the fourth radius of curvature.

9. The method of claim 6, wherein said upper surface portion of said lower part and said lower surface portion of said middle part are configured to allow both rotational and translational movement between said middle part and said lower part, and wherein said lower surface portion of said upper part and said upper surface portion of said middle part are configured to allow rotational but not translational movement between said upper part and said middle part.

10. The method of claim 9, wherein the upper part has a convex lower surface, the lower part has a convex upper surface, and wherein the middle part has an upper concave surface and a lower concave surface.

11. A method of producing a prosthesis for vertebrae comprising:
providing a mathematical model for designing a prosthesis used to simulate kinematics of an intervertebral disk;
using the mathematical model to produce a prosthesis comprising a first part configured to be secured to a first vertebrae, a second part configured to be secured to a second vertebrae, and a middle part positioned between the first part and the second part, which prosthesis simulates kinematics of an intervertebral disk and wherein movement of the first part with respect to the second part when the prosthesis is attached to upper and lower vertebrae simulates rotational and translational movements possible with an intervertebral disk.

12. The method of claim 11, wherein the first part has a first part surface portion with a first radius of curvature, the second part has a second part surface portion with a second radius of curvature, wherein each of the first and second radii of curvature is offset rearwardly with respect to a central vertical axis through the upper and lower parts.

13. The method of claim 11, wherein said second part and said middle part are configured to allow both rotational and translational movement between said second part and said middle part, and wherein said first part and said middle part are configured to allow rotational but not translational movement between said first part and said middle part.

14. The method of claim 13, wherein said first part is an upper part, said second part is a lower part, and wherein the first part has a convex lower surface, the second part has a convex upper surface, and wherein the middle part has an upper concave surface and a lower concave surface.

* * * * *